(12) United States Patent
Kabasawa et al.

(10) Patent No.: US 8,987,690 B2
(45) Date of Patent: Mar. 24, 2015

(54) HIGH-ENERGY ION IMPLANTER

(71) Applicant: SEN Corporation, Tokyo (JP)

(72) Inventors: Mitsuaki Kabasawa, Ehime (JP);
Kazuhiro Watanabe, Ehime (JP);
Haruka Sasaki, Ehime (JP); **Kouji
Kato, Ehime (JP); Hitoshi Ando**, Ehime
(JP)

(73) Assignee: SEN Corporation, Tokyo (JP)

( * ) Notice: Subject to any disclaimer, the term of this patent is extended or adjusted under 35 U.S.C. 154(b) by 0 days.

(21) Appl. No.: 14/287,767

(22) Filed: May 27, 2014

(65) Prior Publication Data

US 2014/0353517 A1 Dec. 4, 2014

(30) Foreign Application Priority Data

May 28, 2013 (JP) ................................ 2013-112036

(51) Int. Cl.
| | |
|---|---|
| *H01J 37/317* | (2006.01) |
| *H01J 37/20* | (2006.01) |
| *C23C 14/48* | (2006.01) |
| *H01J 37/30* | (2006.01) |
| *H01J 37/05* | (2006.01) |
| *A61N 5/10* | (2006.01) |
| *G21K 1/10* | (2006.01) |

(52) U.S. Cl.
CPC .............. *H01J 37/3172* (2013.01); *G21K 1/10* (2013.01); *H01J 37/3007* (2013.01); *H01J 37/05* (2013.01); *A61N 5/1044* (2013.01)
USPC ................ 250/492.21; 250/492.1; 250/492.3; 250/396 R; 250/396 ML; 250/492.23

(58) Field of Classification Search
CPC ..... A61N 5/10; A61N 5/1075; A61N 5/1037; A61N 5/1044; A61N 5/1049; A61N 5/1064; A61N 5/1081; G21K 5/04; G21K 1/10; G21K 1/14; H01J 37/05; H01J 37/3171; H01J 37/3007; H01J 37/32412
USPC .......... 250/492.3, 396 R, 492.21, 397, 492.1, 250/252.1, 336.1, 385.1, 396 ML, 398, 399, 250/423 R, 492.23, 505.1
See application file for complete search history.

(56) References Cited

U.S. PATENT DOCUMENTS 3,838,284 A * 9/1974 McIntyre et al. .......... 250/385.1
6,414,327 B1 * 7/2002 Klinkowstein et al. .. 250/492.21
(Continued)

FOREIGN PATENT DOCUMENTS

| JP | S49-22580 A | 6/1974 |
| JP | 2000-011944 A | 1/2000 |

(Continued)

*Primary Examiner* — David A Vanore
(74) *Attorney, Agent, or Firm* — Rader, Fishman & Grauer PLLC

(57) ABSTRACT

A high-energy ion implanter includes a beam generation unit that includes an ion source and a mass analyzer, a high-energy multi-stage linear acceleration unit, a high-energy beam deflection unit that changes the direction of a high-energy ion beam toward a wafer, and a beam transportation unit that transports the deflected high-energy ion beam to the wafer. The beam transportation unit includes a beam shaper, a high-energy beam scanner, a high-energy beam collimator, and a high-energy final energy filter. Further, the high-energy beam collimator is an electric field type beam collimator that collimates a scan beam while performing the acceleration and the deceleration of a high-energy beam by an electric field.

19 Claims, 19 Drawing Sheets

(56) References Cited

U.S. PATENT DOCUMENTS

| | | | |
|---|---|---|---|
| 6,639,227 B1* | 10/2003 | Glavish et al. | 250/492.2 |
| 7,154,108 B2* | 12/2006 | Tadokoro et al. | 250/492.3 |
| 7,456,415 B2* | 11/2008 | Yanagisawa et al. | 250/492.3 |
| 8,035,080 B2 | 10/2011 | Satoh | |
| 8,039,821 B2* | 10/2011 | Chen | 250/492.21 |
| 8,106,371 B2* | 1/2012 | Fujii et al. | 250/492.3 |
| 8,405,044 B2* | 3/2013 | MacKinnon et al. | 250/396 ML |
| 2004/0002202 A1* | 1/2004 | Horsky et al. | 438/515 |
| 2004/0200983 A1* | 10/2004 | Fujimaki et al. | 250/492.3 |
| 2005/0087700 A1* | 4/2005 | Tadokoro et al. | 250/492.21 |
| 2006/0226372 A1* | 10/2006 | Yanagisawa et al. | 250/396 R |
| 2007/0252093 A1* | 11/2007 | Fujimaki et al. | 250/492.3 |
| 2010/0237260 A1* | 9/2010 | Chen | 250/492.3 |
| 2011/0017920 A1* | 1/2011 | Goer et al. | 250/396 R |
| 2013/0221213 A1* | 8/2013 | Takayanagi et al. | 250/252.1 |
| 2014/0048727 A1* | 2/2014 | Huntzinger et al. | 250/503.1 |
| 2014/0150723 A1* | 6/2014 | Kabasawa et al. | 118/723 R |

FOREIGN PATENT DOCUMENTS

| | | |
|---|---|---|
| JP | 3302436 B2 | 7/2002 |
| JP | 3374335 B2 | 2/2003 |
| JP | 2003-288857 A | 10/2003 |
| JP | 2004-508680 A | 3/2004 |
| WO | WO-02/21565 A2 | 3/2002 |

* cited by examiner

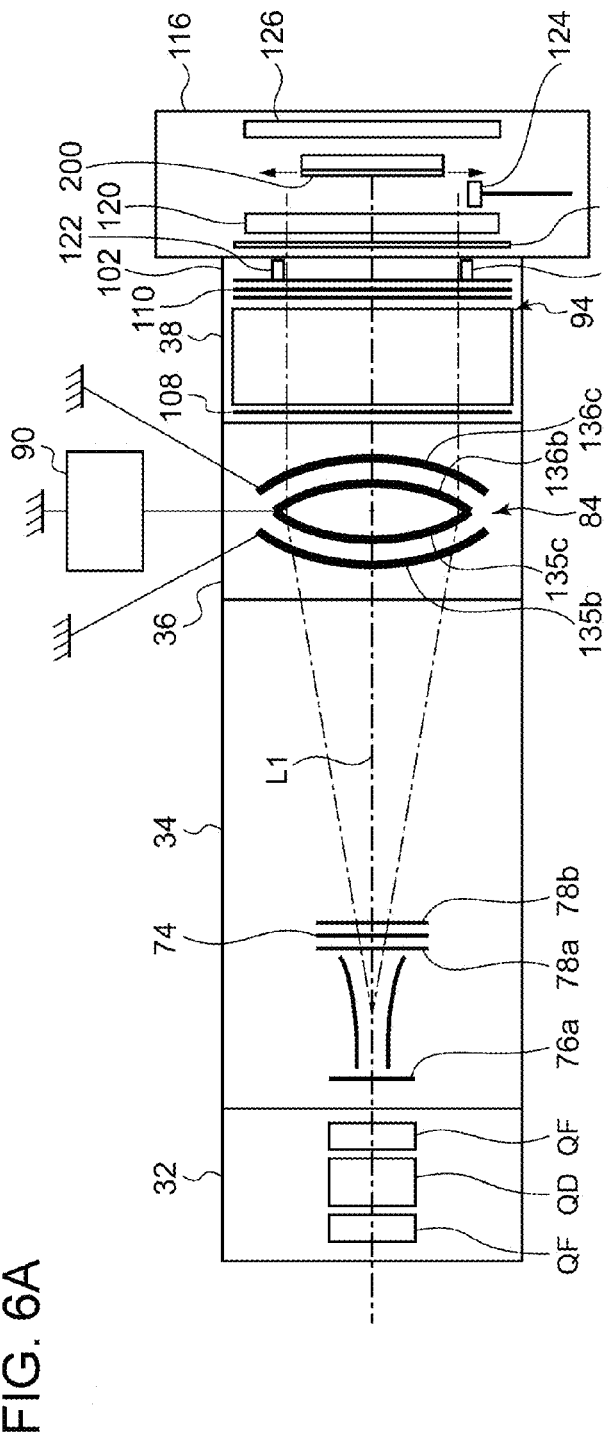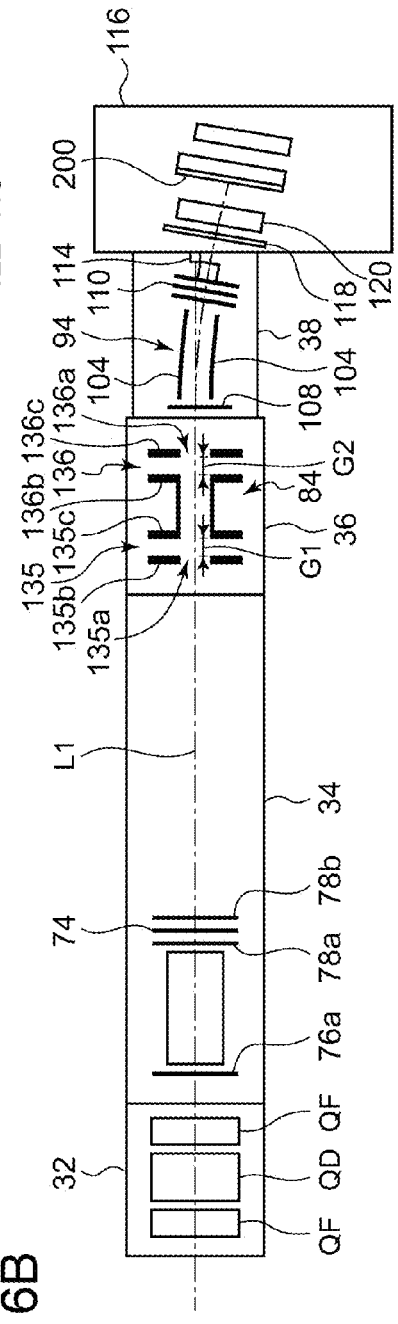

24,30

24,30

HIGH-ENERGY ION IMPLANTER

BACKGROUND OF THE INVENTION

1. Field of the Invention

The present invention relates to a high-energy ion implanter.

2. Description of the Related Art

In a semiconductor device production process, an important process is generally performed in which ions are implanted into a semiconductor wafer in a vacuum state so as to add impurities to crystals of the semiconductor wafer. Accordingly, a conductive property is changed so that the semiconductor wafer becomes a semiconductor device. An apparatus used in this process is generally called an ion implanter that accelerates impurity atoms as ions for the semiconductor device and implants impurity atoms into the semiconductor wafer.

Hitherto, an apparatus for performing a high-energy ion implantation by further deeply implanting an ion beam into the semiconductor wafer has been used with the high integration and the high performance of the semiconductor device. Such an apparatus is particularly called a high-energy ion implanter. As an example, there is known a method of configuring an ion beam acceleration system by a tandem type electrostatic accelerator.

(Batch Type)

Further, a batch treatment type high-energy ion implanter with a radio frequency linear accelerator for performing a radio frequency acceleration has been used for many years.

The batch treatment type ion implantation is a method of uniformly implanting ions into wafers while several tens of silicon wafers are loaded on the outer periphery of an aluminum disk having a diameter of about 1 m and the disk is rapidly rotated by 1000 revolutions per minute. In order to prevent the pop-out state of the wafer by a centrifugal force, the wafer loading portion of the disk has an angle of about 5° with respect to a rotation surface (a surface perpendicular to a rotation shaft). The batch treatment type ion implantation method has a problem in which an implantation angle (an angle at which the ions are incident to the wafer) is different by about 1° between the center and the end of the wafer (the implantation angle deviation) due to the above-described angle and the rotation of the wafer.

In general, a die on the wafer has anion implantation performing region and a non-ion implantation performing region, and the non-ion implantation performing region is covered by an organic substance called a photoresist. Since the ions do not need to penetrate the photoresist during the implantation, the photoresist to be coated during the high-energy ion implantation is much thickened. In the ion implantation performing region, the photoresist is excluded by lithography. However, when the integration degree is high and the implantation region is minute, the ions are perpendicularly implanted to a bottom of a deep hole surrounded by an upright photoresist wall. In the ion implantation in the structure having a high aspect ratio, the high precision of implantation angle is demanded.

In particular, in a case where a high-quality imaging device such as a CCD is produced, the resolution increases with the deep ion implantation, and hence the sensitivity is improved. For this reason, a super-high-energy ion implantation (3 to 8 MeV) is also performed. In this case, the allowed implantation angle error is about 0.1°, and a batch type apparatus with a large implantation angle deviation may not be used.

(Single Wafer Type High-Energy Ion Implanter)

Therefore, a single wafer type high-energy ion implanter has been practically realized in recent years. In the batch type, the ion beam is uniformly implanted in the horizontal direction in a manner such that the beam is fixed and the wafer moves (the rotation on the disk). On the contrary, in the single wafer type, the beam moves (so that the beam scans in the horizontal direction) and the wafer is fixed. In this type, when the scan beam is collimated, the implantation dose may be uniform within the wafer surface, and the implantation angle may be also uniform. Accordingly, the problem of the implantation angle deviation may be solved. Furthermore, the dose uniformity in the vertical direction is realized by moving the wafer at a constant velocity in both types, but the angle error does not occur in accordance with the movement.

In addition, since the single wafer type ion implanter does not uselessly consume the silicon wafer when a small number of wafers are treated, the single wafer type ion implanter is suitable for a small lot multi-product production, and hence a demand therefor has been increased in recent years.

Here, in the production of the high-quality imaging device, there is a need to meet various difficult demands in which the angle precision is needed, the metal contamination needs to be removed, the implantation damage (the residual crystal defect after the annealing) needs to be small, and the implantation depth precision (the energy precision) needs to be good. Accordingly, even the single wafer type ion implanter has many points to be improved.

In the single wafer type high-energy ion implanter of the related art, the tandem type electrostatic accelerator or the radio frequency acceleration type heavy ion linac (the linear accelerator) has been used as the high energy acceleration type.

The downstream side of the acceleration system is provided with an energy filtering magnet, a beam scanner, and a parallel (parallelization) magnet that collimates a scan orbit by a magnetic field. Then, the beam has the same incident angle (implantation angle) with respect to the wafer at any scan position due to the parallel magnet. The ion energy is up to about 3 to 4 MeV.

Further, in a part of the (single wafer type) medium current ion implanter used in the energy region (10 to 600 keV) lower than that of the high-energy ion implanter, an electric field parallel lens is used which collimates the scan orbit by the electric field (the electrode). Since the electric field parallel lens may collimate the scan orbit while keeping the symmetry of the orbit, the angle precision is more critically treated compared to the parallel magnet. Further, in this apparatus, an electric field type deflection electrode called an AEF (Angular Energy Filter) is attached to the vicinity of the wafer. Since the ions subjected to a change in charge state during the transportation of the beam or the particles generated in the beamline are removed by the AEF, a highly pure beam may be supplied.

SUMMARY OF THE INVENTION

The invention is made in view of such circumstances, and an object thereof is to provide a high-energy ion implanter that highly precisely collimates a scanned high-energy ion beam.

In order to solve the above-described problems, a high-energy ion implanter according to an aspect of the invention is a high-energy ion implanter that accelerates an ion beam extracted from an ion source, transports the ion beam to a wafer along a beamline, and implants the ion beam into the wafer. This apparatus includes: a beam generation unit that includes the ion source and a mass analyzer; a high-energy multi-stage linear acceleration unit that accelerates an ion beam so as to generate a high-energy ion beam; a high-energy beam deflection unit that changes the direction of the high-energy ion beam toward the wafer; a beam transportation line unit that transports the deflected high-energy ion beam to the wafer; and a substrate processing/supplying unit that uniformly implant the transported high-energy ion beam into the semiconductor wafer. The beam transportation unit includes a beam shaper, a high-energy beam scanner, a high-energy beam collimator, and a high-energy final energy filter. Further, the high-energy ion beam emitted from the deflection unit is scanned at both sides of the reference trajectory of the beamline by the beam scanner and is collimated by the beam collimator so that mixed ions which are different in any one of the mass, the ion charge state, and the energy are implanted to the wafer by the high-energy final energy filter. Further, the high-energy beam collimator is an electric field type beam collimator that collimates the scan beam while performing the acceleration and the deceleration of the high-energy beam by the electric field.

BRIEF DESCRIPTION OF THE DRAWINGS

FIG. 6A is a top view illustrating a schematic configuration from a beam scanner to a substrate processing/supplying unit along a beamline after a beam collimator, and FIG. 6B is a side view illustrating a schematic configuration from a beam scanner to a substrate processing/supplying unit along a beamline after a beam collimator;

DETAILED DESCRIPTION OF THE INVENTION

Figure 1:
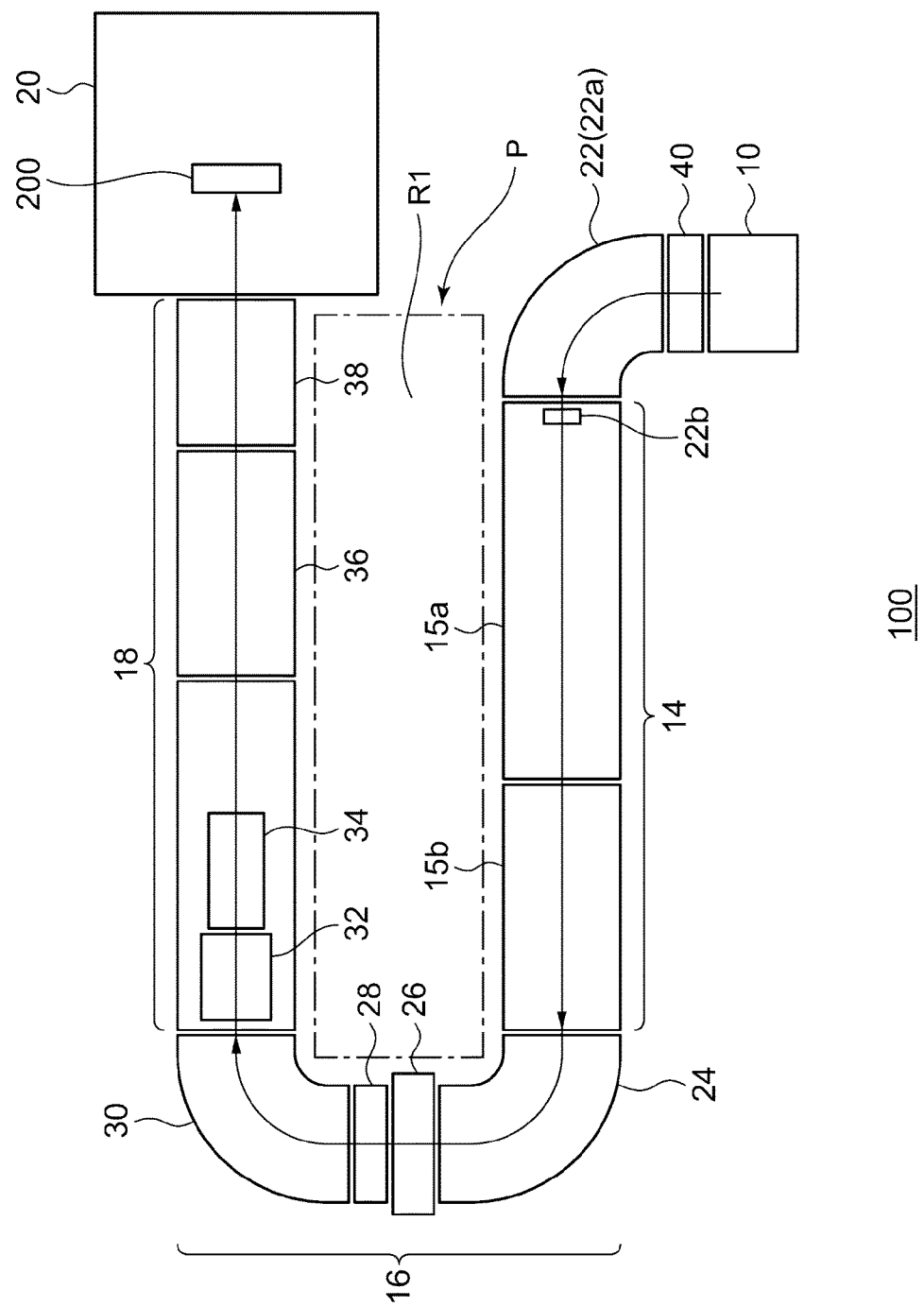
FIG. 1 is a schematic view illustrating a schematic layout and a beamline of a high-energy ion implanter according to an embodiment.

The invention will now be described by reference to the preferred embodiments. This does not intend to limit the scope of the present invention, but to exemplify the invention.

Hereinafter, an example of a high-energy ion implanter according to the embodiment will be described in detail. First, the reason why the invention is contrived by the present inventor and the like will be described.

(Parallel Magnet)

The following problems arise in a high-energy ion implanter of the related art that employs a parallel (collimate) magnet which parallelizes (collimates) an orbit by a deflection magnetic field.

When a high-energy ion is implanted into a photoresist-coated wafer, a large amount of an outgas is generated. Then, an interaction occurs between molecules of the outgas and beam ions, and hence the charge state of some ions change. When a change in valance occurs while the beam passes through the parallel magnet, a deflection angle changes and the parallelism of the beam is collapsed. Accordingly, an implantation angle with respect to the wafer is not uniform.

Further, the amount (the number or the dose) of the implanted ions may be obtained by measuring a beam current in a faraday cup disposed near the wafer. However, the measurement value is influenced due to a change in charge state, and hence the measurement value is deviated from a predetermined implantation dose. As a result, the expected characteristics of a semiconductor device may not be obtained according to the design.

Further, in the parallelism of one parallel magnet, the inner and outer orbits have different deflection angles and different orbit lengths. For this reason, the ratio of the ions subjected to a change in charge state increases as it goes toward the outer orbit, and hence the dose uniformity inside the wafer surface is also degraded.

Thus, a recent demand for highly precise implantation may not be sufficiently handled by the beam transportation type of the high-energy ion implanter of the related art.

Further, the parallel magnet needs a wide magnetic pole in the scan direction and a parallelizing section having a certain length. Since the length and the size of the magnetic pole increase when the energy increases, the weight of the parallel magnet considerably increases. In order to stably fix and hold the apparatus, the design for the strength of the semiconductor factory needs to be reinforced, and the power consumption considerably increases.

These problems may be solved when the electric field collimating lens and the electric field (the electrode type)

energy filter (AEF: Angular Energy Filter) used in the above-described medium current ion implanter may be used in the high-energy region. The electric field collimating lens aligns and collimates the scan orbit to the center orbit while keeping the symmetry of the orbit, and the AEF removes the ions subjected to a change in charge state directly before the wafer. Accordingly, even when a large amount of the outgas exists, a beam without an energy contamination may be obtained, and hence the implantation angle in the scan direction does not become non-uniform as in the case of the parallel magnet. As a result, the ions may be implanted with an accurate implantation distribution in the depth direction and a uniform implantation dose, and the implantation angle also becomes uniform, thereby realizing a highly precise ion implantation. Further, since the light-weight electrode member is used, the power consumption may be decreased compared to the electromagnet.

The point of the invention is to obtain an apparatus capable of performing the same highly precise implantation as that of the medium current apparatus in the high-energy apparatus by introducing an excellent system of the medium current ion implanter into the high-energy ion implanter. The problems to be solved in this trial will be described below. The first problem is the length of the apparatus.

In a case where the ion beams are deflected at the same trajectory, the necessary magnetic field is proportional to the square root of the energy, and the necessary electric field is proportional to the energy. Thus, the length of the deflection magnetic pole is proportional to the square root of the energy, and the length of the deflection electrode is proportional to the energy. When the highly precise angle implantation is tried by mounting the electric field collimating lens and the electric field AEF onto the high-energy ion implanter, the beam transportation system (the distance from the scanner to the wafer) largely increases in length compared to the apparatus of the related art that uses the parallel magnet.

For example, as the high-energy ion implanter that includes a parallelization mechanism using such an electric field, a structure is considered which is obtained by substantially linearly fixing constituents such as an ion source, a mass analysis magnet, a tandem type electrostatic accelerator or a radio frequency linear accelerator, a beam scanner, a scan orbit parallelization device, an energy filter, an implantation process chamber, and a substrate transportation unit (an end station) as in the case of the high-energy ion implanter of the related art. In this case, the entire length of the apparatus increase by about 20 m compared to the apparatus of the related art having a length of about 8 m. Accordingly, it takes large effort when the installation place is set and prepared and the installation operation is performed, and then the installation area also increases. Further, a work space is also needed for the alignment adjustment of the devices and the maintenance, the repair, or the adjustment thereof after the operation of the apparatus. Such a large ion implanter may not satisfy a demand for adjusting the size of the apparatus in the semiconductor production line to the actual size of the apparatus arranged in the factory production line.

In view of such circumstances, an object of the beamline structure in the aspect of the invention is to provide a highly precise high-energy ion implanter with an electric field collimating lens and an electric field energy filter by simplifying and efficiently adjusting an installation place setting and preparing work, an installation work, or a maintenance work while ensuring a sufficient work area and realizing a technique of suppressing an increase in installation area.

(U-Shaped Folded Beam Line)

The object may be attained by a configuration in which the beamline of the high-energy ion implanter includes a long line portion that is formed by a plurality of units for accelerating an ion beam generated by an ion source and a long line portion that is formed by a plurality of units for adjusting and implanting a scan beam into a wafer and a horizontal U-shaped folded beamline having the long line portions facing each other is formed. Such a layout is realized by substantially matching the length of the beam transportation unit including a beam scanner, a beam collimator, an energy filter, and the like to the length of the unit accelerating the ions from the ion source. Then, a sufficiently wide space is provided between two long line portions for the maintenance work.

An aspect of the invention is obtained on the basis of the layout of the beamline, and an object of the invention is to provide a high-energy ion implanter which collimates a scanned high-energy ion beam in a bilaterally symmetric state by an electric field and performs a highly precise ion implantation in an environment with a large amount of an outgas.

A high-energy ion implanter according to an aspect of the invention is a high-energy ion implanter that accelerates ions generated from an ion source so as to generate an ion beam, transports the ion beam to a wafer along a beamline, and implants the ion beam into the wafer, and includes: a beam generation unit that includes the ion source and a mass analyzer; a high-energy multi-stage linear acceleration unit that accelerates an ion beam so as to generate a high-energy ion beam; a high-energy beam deflection unit that changes the direction of the high-energy ion beam toward the wafer; a high-energy beam transportation unit that transports the deflected high-energy ion beam to the wafer; and a substrate processing/supplying unit that uniformly implants the transported high-energy ion beam into the semiconductor wafer. The beam transportation unit includes a beam shaper, a high-energy beam scanner, a high-energy beam collimator, and a high-energy final energy filter. Then, the high-energy ion beam emitted from the deflection unit is scanned at both sides of the reference trajectory of the beamline by the beam scanner, and is collimated to the reference trajectory of the orbits of the scan beams while the bilateral symmetric is maintained by the beam collimator, mixed ions which are different in the mass, the ion charge state, the energy, and the like are removed by the final energy filter, and the resultant ions are implanted into the wafer. The high-energy beam collimator includes a pair of acceleration electrodes that accelerates the ion beam and deflects the ion beam toward the reference trajectory and a pair of deceleration electrodes that decelerates the ion beam and deflects the ion beam toward the reference trajectory. Here, the high-energy beam collimator is configured as an acceleration-deceleration electrode lens group that includes at least two sets or more of the pair of acceleration electrodes and the pair of deceleration electrodes.

According to the aspect of the invention, the scanned high-energy ion beam may be collimated in a bilaterally symmetric state. Accordingly, even in a state where a large amount of the outgas exists, the ion beam may be implanted with a uniform implantation dose and a uniform implantation angle, and hence the highly precise ion implantation is realized. Further, a light-weight electrode member is used. The power consumption may be decreased compared to the electromagnet.

Therefore, the high-energy ion implanter according to the aspect of the embodiment is an ion implanter that accelerates the ions generated by the ion source, transports the ions as the ion beam along the beamline to the wafer, and implants the ions into the wafer. This apparatus includes the high-energy multi-stage linear acceleration unit that accelerates the ion beam so as to generate the high-energy ion beam, the deflection unit that changes the direction of the orbit of the high-energy ion beam toward the wafer, and the beam transportation line unit that transports the deflected high-energy ion beam to the wafer, and the collimated ion beam is highly precisely irradiated to the wafer moving in a mechanical scan state so as to be implanted into the wafer.

The high-energy ion beam that is emitted from the radio frequency (AC-type) high-energy multi-stage linear acceleration unit for highly accelerating the ion beam includes a certain range of energy distribution. For this reason, in order to scan and collimate the high-energy ion beam of the rear stage and irradiate the high-energy ion beam to the wafer moving in a mechanical scan state, there is a need to perform the highly precise energy analysis, the center orbit correction, and the beam convergence and divergence adjustment in advance.

The beam deflection unit includes at least two highly precise deflection electromagnets, at least one energy width confining slit, an energy analysis slit, and at least one lateral convergence unit. The plurality of deflection electromagnets are formed so as to perform the energy analysis of the high-energy ion beam, the precise correction of the ion implantation angle, and the suppression of the energy dispersion. In the highly precise deflection electromagnets, a nuclear magnetic resonance probe and a hall probe are attached to the electromagnet for the energy analysis, and only the hall probe is attached to the other electromagnet. The nuclear magnetic resonance probe is used to calibrate the hall probe, and the hall probe is used for the uniform magnetic field feedback control.

The beam transportation line unit may implant ions by scanning and parallelizing the high-energy ion beam and highly precisely irradiating the high-energy ion beam to the wafer moving in a mechanical scan state.

Hereinafter, an example of the high-energy ion implanter according to the embodiment will be described in more detail with reference to the drawings. Furthermore, the same reference numerals will be given to the same components in the description of the drawings, and the repetitive description of the same components will be appropriately omitted. Further, the configuration mentioned below is merely an example, and does not limit the scope of the invention.

(High-Energy Ion Implanter)

First, a configuration of the high-energy ion implanter according to the embodiment will be simply described. Furthermore, the content of the specification may be applied to not only the ion beam as one of kinds of charged particles, but also the apparatus involved with the charged particle beam.

FIG. 1 is a schematic view illustrating a schematic layout and a beamline of a high-energy ion implanter 100 according to the embodiment.

The high-energy ion implanter 100 according to the embodiment is an ion implanter that includes a radio frequency linear acceleration type ion accelerator and a high-energy ion transportation beamline, and is configured to accelerate ions generated by an ion source 10, transports the ions along the beamline to a wafer (a substrate) 200 as an ion beam, and implants the ions into a wafer 200.

As illustrated in FIG. 1, the high-energy ion implanter 100 includes an ion beam generation unit 12 that generates ions and separates the ions by mass, a high-energy multi-stage linear acceleration unit 14 that accelerates an ion beam so as to become a high-energy ion beam, a beam deflection unit 16 that performs an energy analysis, a center orbit correction, and an energy dispersion control on the high-energy ion beam, a beam transportation line unit 18 that transports the analyzed high-energy ion beam to a wafer, and a substrate processing/supplying unit 20 that uniformly implant the transported high-energy ion beam into the semiconductor wafer.

The ion beam generation unit 12 includes the ion source 10, an extraction electrode 40, and a mass spectrometer 22. In the ion beam generation unit 12, a beam is extracted from the ion source 10 through the extraction electrode and is accelerated, and the extracted and accelerated beam is subjected to a mass analysis by the mass spectrometer 22. The mass spectrometer 22 includes a mass analysis magnet 22a and a mass analysis slit 22b. There is a case in which the mass analysis slit 22b is disposed directly behind the mass analysis magnet 22a. However, in the embodiment, the mass analysis slit is disposed inside the entrance of the high-energy multi-stage linear acceleration unit 14 as the next configuration.

Only the ions necessary for the implantation are selected as a result of the mass analysis using the mass spectrometer 22, and the ion beam of the selected ions is led to the next high-energy multi-stage linear acceleration unit 14. The direction of the ion beam that is further accelerated by the high-energy multi-stage linear acceleration unit 14 is changed by the beam deflection unit 16.

The beam deflection unit 16 includes an energy analysis electromagnet 24, a lateral convergence quadrupole lens 26 that suppresses an energy dispersion, an energy width confining slit 27 (see FIGS. 5A and 5B below), an energy analysis slit 28, and a deflection electromagnet 30 having a steering function. Furthermore, the energy analysis electromagnet 24 may be called an energy filter electromagnet (EFM). The direction of the high-energy ion beam is changed by the deflection unit so as to be directed toward the substrate wafer.

The beam transportation line unit 18 is used to transport the ion beam emitted from the beam deflection unit 16, and includes a beam shaper 32 formed by a convergence/divergence lens group, a beam scanner 34, a beam collimator 36, and a final energy filter 38 (with a final energy separation slit). The length of the beam transportation line unit 18 is designed so as to match the lengths of the ion beam generation unit 12 and the high-energy multi-stage linear acceleration unit 14, and the beam transportation line unit 18 is connected to the beam deflection unit 16 so as to form a U-shaped layout as a whole.

The substrate processing/supplying unit 20 is provided at the termination end of the downstream side of the beam transportation line unit 18, and the implantation process chamber accommodates a beam monitor that measures the beam current, the position, the implantation angle, the convergence and divergence angle, the vertical and horizontal ion distribution, and the like of the ion beam, a charge prevention device that prevents the charge of the substrate by the ion beam, a wafer transportation mechanism that carries the wafer (the substrate) 200 and installs the wafer at an appropriate position and an appropriate angle, an ESC (Electro Static Chuck) that holds the wafer during the ion implantation, and a wafer scan mechanism that operates the wafer in a direction perpendicular to the beam scan direction at the velocity in response to a change in the implantation beam current.

In this way, the high-energy ion implanter 100 that is formed by arranging the units in a U-shape ensures satisfactory workability while suppressing an increase in foot print. Further, in the high-energy ion implanter 100, the units or the devices are formed as a module, and hence may be attached, detached, and assembled in accordance with the beamline reference position.

Next, the units and the devices constituting the high-energy ion implanter 100 will be described further in detail.

(Ion Beam Generation Unit)

Figure 2A:
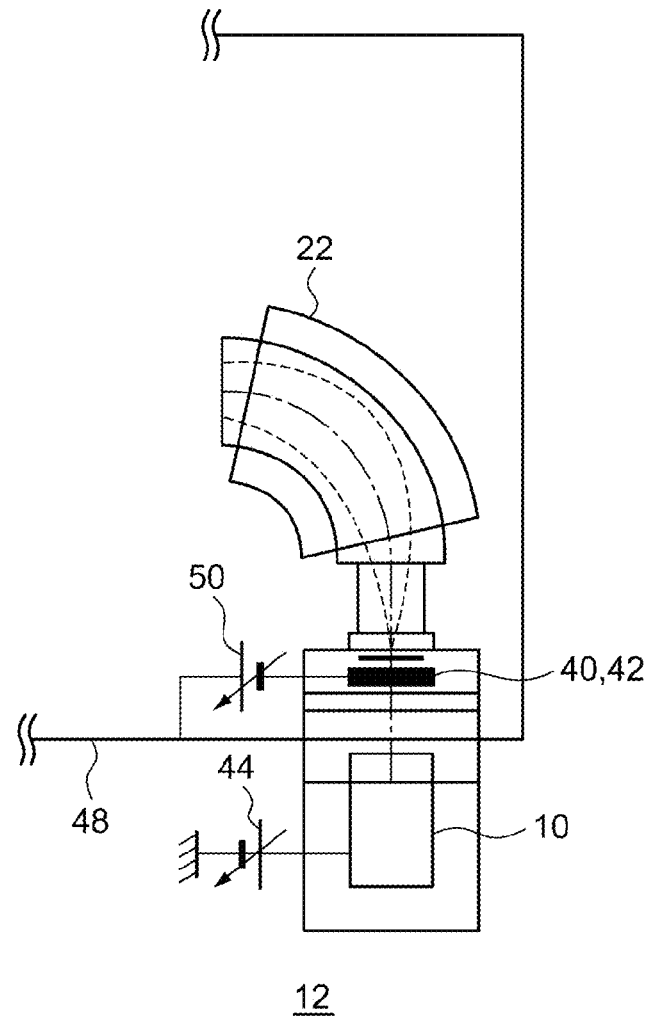
FIG. 2A is a top view illustrating a schematic configuration of an ion beam generation unit.
Figure 2B:
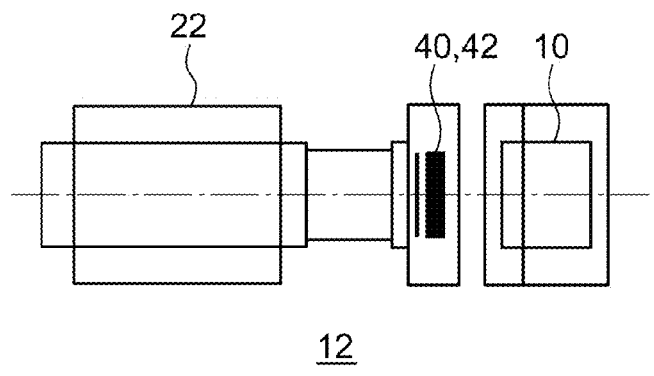
FIG. 2B is a side view illustrating the schematic configuration of the ion beam generation unit.

FIG. 2A is a top view illustrating a schematic configuration of the ion beam generation unit, and FIG. 2B is a side view illustrating a schematic configuration of the ion beam generation unit.

As illustrated in FIGS. 2A and 2B, the extraction electrode 40 that extracts an ion beam from plasma generated inside an ion chamber (an arc chamber) is provided at the exit of the ion source 10 disposed at the most upstream side of the beamline. An extraction suppression electrode 42 that suppresses electrons included in the ion beam extracted from the extraction electrode 40 from reversely flowing toward the extraction electrode 40 is provided near the downstream side of the extraction electrode 40.

The ion source 10 is connected to an ion source high-voltage power supply 44. An extraction power supply 50 is connected between the extraction electrode 40 and a terminal 48. The downstream side of the extraction electrode 40 is provided with the mass spectrometer 22 that separates predetermined ions from the incident ion beam and extracts the separated ion beam.

Figure 5A:
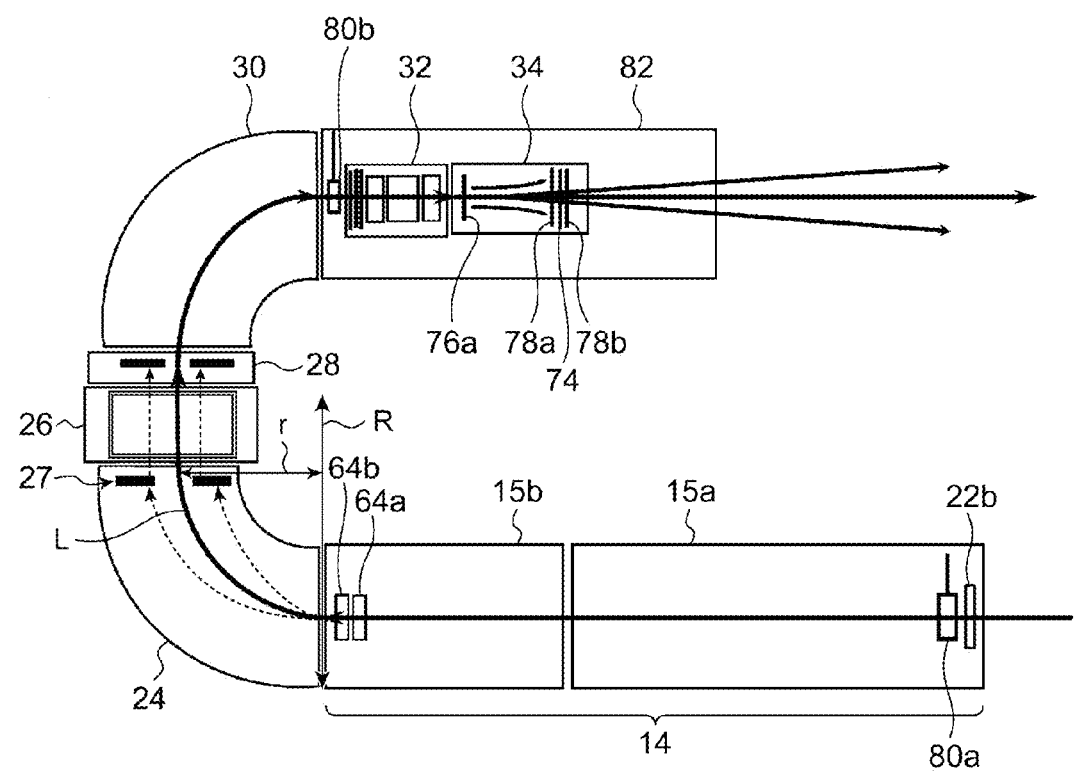
FIGS. 5A and 5B are top views illustrating a schematic configuration of an EFM (an energy analyzing deflection electromagnet), an energy width confining slit, an energy analysis slit, a BM (a lateral center orbit correcting deflection electromagnet), a beam shaper, and a beam scanner (a scanner)
Figure 5B:
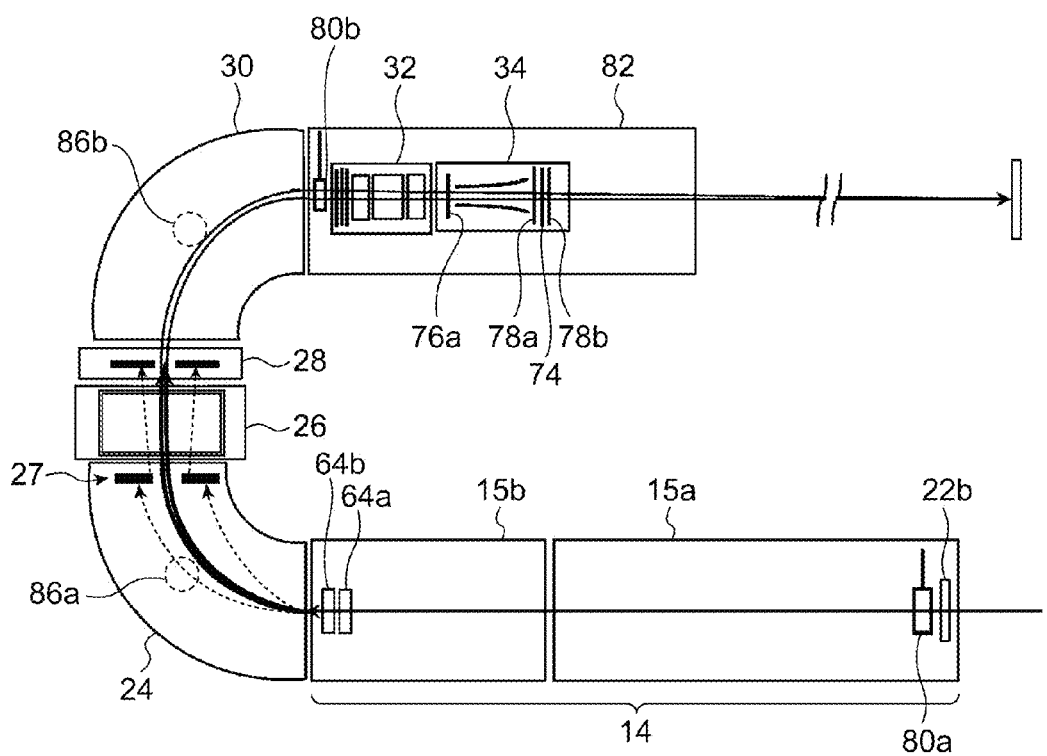

As illustrated in FIGS. 5A and 5B to be described below, a faraday cup (for an injector) 80a that measures the total beam current of the ion beam is disposed at the foremost portion inside the linear acceleration portion housing of the high-energy multi-stage linear acceleration unit 14.

Figure 14A:
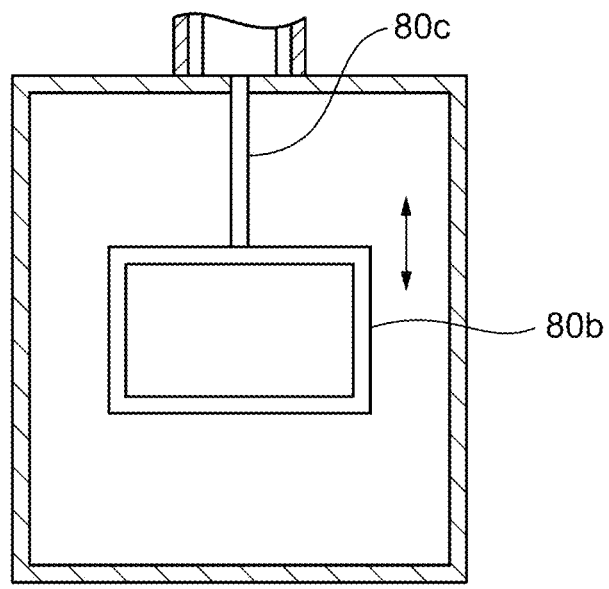
FIG. 14A is a schematic front view illustrating a resolver-faraday cup having substantially the same configuration as that of an injector faraday cup.
Figure 14B:
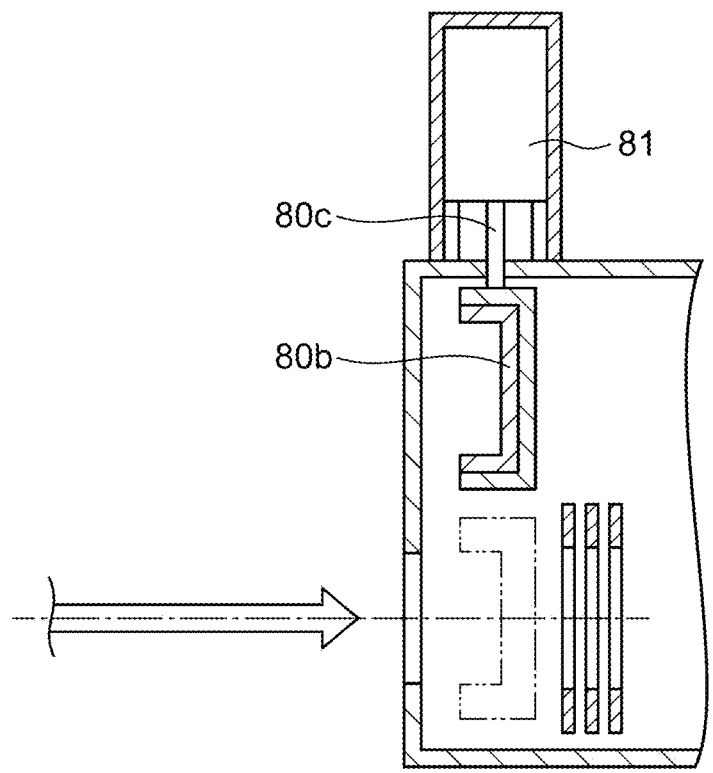
FIG. 14B is a schematic view illustrating an operation of the resolver-faraday cup.

FIG. 14A is a schematic front view illustrating a resolver-faraday cup 80b having substantially the same configuration as that of the injector faraday cup 80a, and FIG. 14B is a schematic view illustrating an operation of the resolver-faraday cup 80b.

The injector faraday cup 80a may be extracted from the vertical direction on the beamline by a driving mechanism, and is formed so that an opening faces the upstream side of the beamline while having a rectangular square shape in the horizontal direction. Accordingly, the injector faraday cup is used to completely interrupt the ion beam reaching the downstream side of the beamline on the beamline if necessary other than the function of measuring the total beam current of the ion beam during the adjustment of the ion source or the mass analysis electromagnet. Further, as described above, the mass analysis slit 22b is disposed inside the entrance of the high-energy multi-stage linear acceleration unit 14 directly before the injector faraday cup 80a. Further, in accordance with the single mass analysis slit or the degree of the mass, a plurality of slits having different widths may be selected or the mass slit width may be changed continuously or step-wisely.

(High-Energy Multi-Stage Linear Acceleration Unit)

Figure 3:
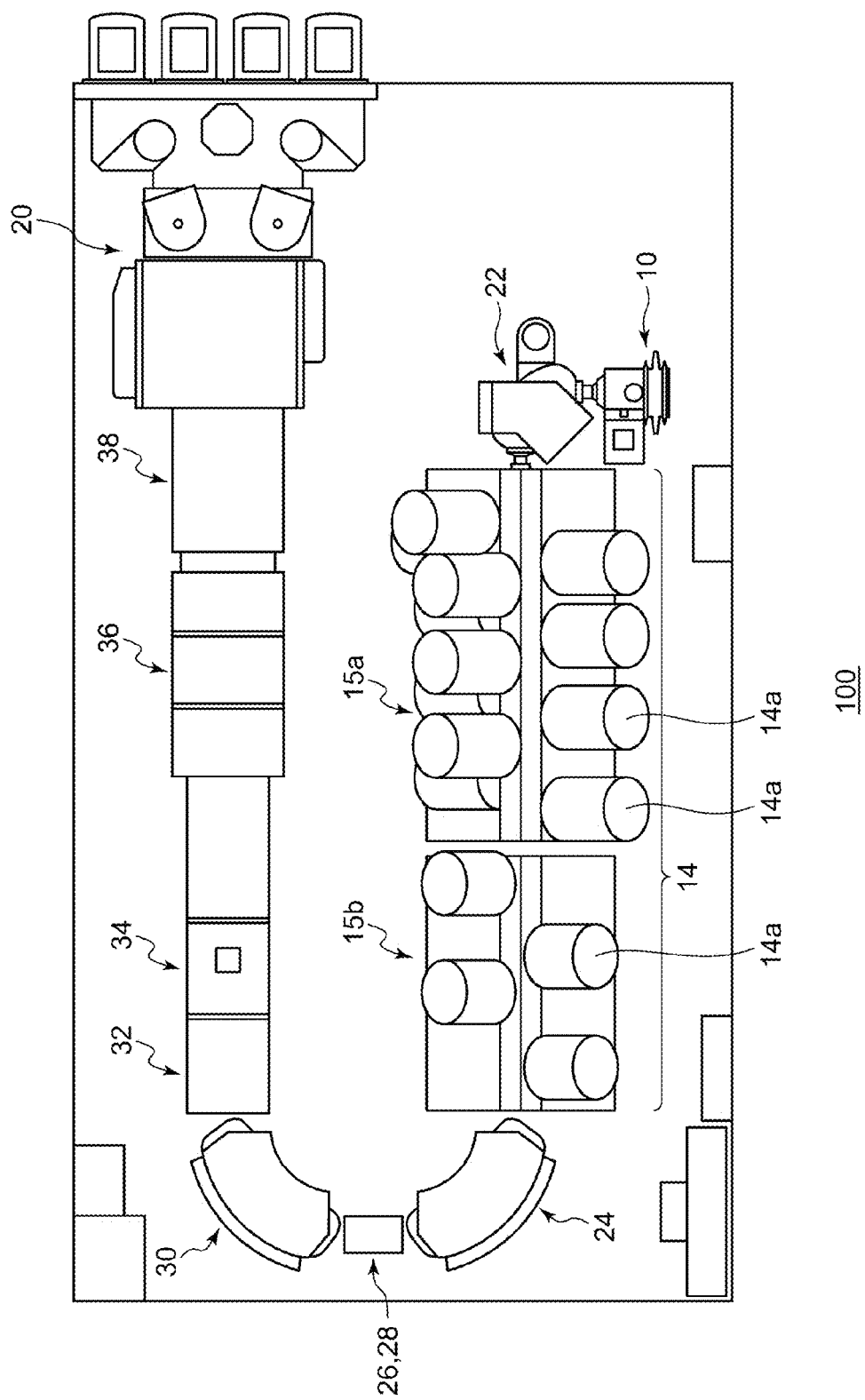
FIG. 3 is a top view illustrating an entire layout including a schematic configuration of a high-energy multi-stage linear acceleration unit.

FIG. 3 is a top view illustrating the entire layout including the schematic configuration of the high-energy multi-stage linear acceleration unit 14. The high-energy multi-stage linear acceleration unit 14 includes a plurality of linear accelerators for accelerating the ion beam, that is, an acceleration gap that interposes one or more radio frequency resonators 14a. The high-energy multi-stage linear acceleration unit 14 may accelerate the ions by the action of the radio frequency (RF) electric field. In FIG. 3, the high-energy multi-stage linear acceleration unit 14 includes a first linear accelerator 15a that includes a basic multi-stage radio frequency resonator 14a for a high-energy ion implantation and a second linear accelerator 15b that includes an additional multi-stage radio frequency resonator 14a for a super-high-energy ion implantation.

Meanwhile, in the ion implanter that uses the acceleration of the radio frequency (RF), the amplitude V [kV] and the frequency f [Hz] of the voltage need to be considered as the parameter of the radio frequency. Further, in a case where a multi-stage radio frequency acceleration is performed, the phase φ [deg] of the radio frequency is added as the parameter. In addition, a magnetic field lens (for example, a quadrupole electromagnet) or an electric field lens (for example, an electric field quadrupole electrode) is needed so as to control the expansion of the ion beam in the vertical and horizontal directions during or after the acceleration by the convergence and divergence effect. Then, the optimal values of these operation parameters are changed by the ion energy passing therethrough, and the strength of the acceleration electric field influences the convergence and divergence action. For this reason, these values are determined after the parameter of the radio frequency is determined.

Figure 4:
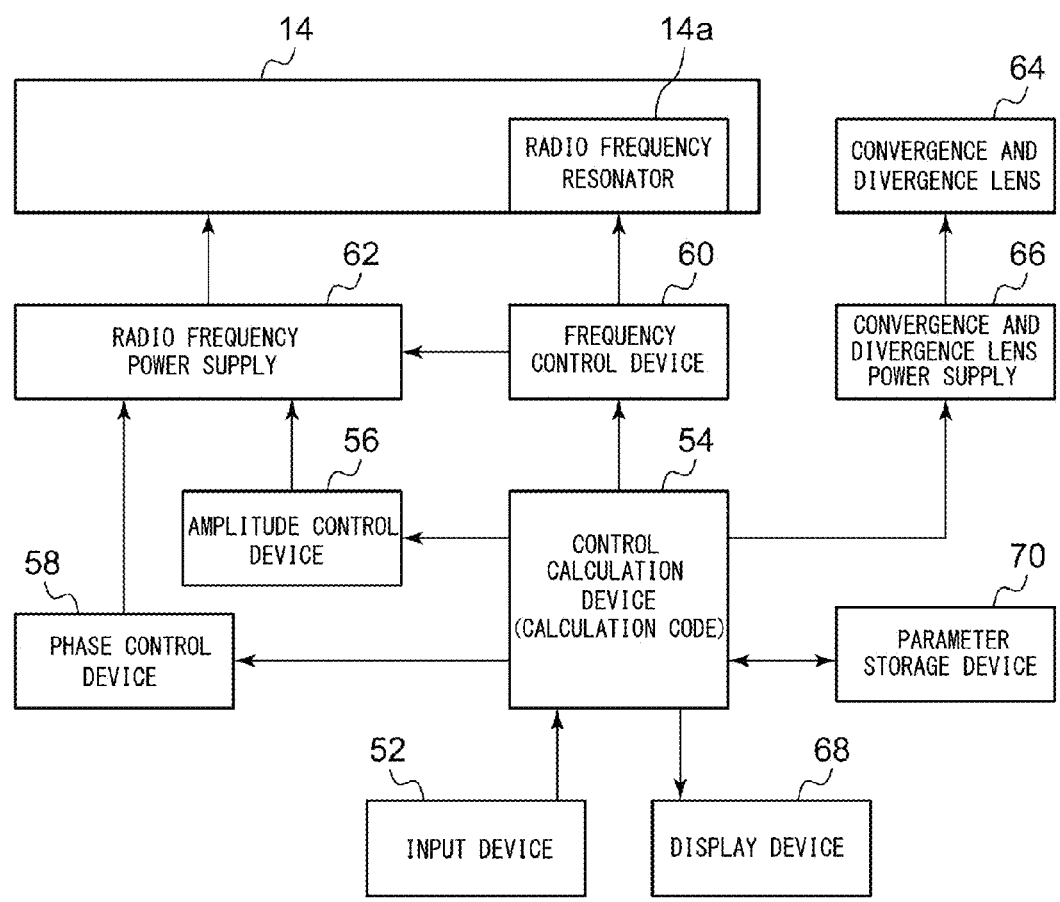
FIG. 4 is a block diagram illustrating a configuration of a control system of a convergence and divergence lens and the high-energy multi-stage linear acceleration unit obtained by linearly arranging acceleration electric fields (gaps) of front ends of a plurality of radio frequency resonators.

FIG. 4 is a block diagram illustrating a configuration of a control system of the convergence and divergence lens and the high-energy multi-stage linear acceleration unit obtained by linearly arranging the acceleration electric fields (the gaps) at the front ends of the plurality of radio frequency resonators.

The high-energy multi-stage linear acceleration unit 14 includes one or more radio frequency resonators 14a. As the components necessary for the control of the high-energy multi-stage linear acceleration unit 14, an input device 52 for allowing an operator to input a necessary condition, a control calculation device 54 that numerically calculates various parameters from the input condition and controls the components, an amplitude control device 56 that adjusts the voltage amplitude of the radio frequency, a phase control device 58 that adjusts the phase of the radio frequency, a frequency control device 60 that controls the frequency of the radio frequency, a radio frequency power supply 62, a convergence and divergence lens power supply 66 for a convergence and divergence lens 64, a display device 68 that displays an operation parameter thereon, and a storage device 70 that stores the determined parameter are needed. Further, the control calculation device 54 stores therein a numerical calculation code (a program) for numerically calculating various parameter in advance.

In the control calculation device 54 of the radio frequency linear accelerator, radio frequency parameters (an amplitude, a frequency, and a phase of a voltage) are calculated so as to obtain the optimal transportation efficiency by simulating the acceleration, the convergence, and the divergence of the ion beam based on the input condition and the numerical calculation code stored therein. Also, the parameter (a Q coil current or a Q electrode voltage) of the convergence and divergence lens 64 that is used to efficiently transport the ion beam is also calculated. The calculated various parameters are displayed on the display device 68. The display device 68 displays a non-answerable mark for the acceleration condition that exceeds the ability of the high-energy multi-stage linear acceleration unit 14.

The voltage amplitude parameter is transmitted from the control calculation device 54 to the amplitude control device 56, and the amplitude control device 56 adjusts the amplitude of the radio frequency power supply 62. The phase parameter is transmitted to the phase control device 58, and the phase control device 58 adjusts the phase of the radio frequency power supply 62. The frequency parameter is transmitted to the frequency control device 60. The frequency control device 60 controls the output frequency of the radio frequency power supply 62, and controls the resonance frequency of the radio frequency resonator 14a of the high-energy multi-stage linear acceleration unit 14. Further, the control calculation device 54 controls the convergence and divergence lens power supply 66 by the calculated convergence and divergence lens parameter.

The convergence and divergence lens 64 that is used to efficiently transport the ion beam is disposed as many as needed at a position inside the radio frequency linear accelerator or a position before and behind the radio frequency linear accelerator. That is, the divergence lens and the convergence lens are alternately provided at the position before and behind the acceleration gap of the front end of the multi-stage radio frequency resonator 14a. At one side thereof, an additional longitudinal convergence lens 64b (see FIGS. 5A and 5B) is disposed behind the lateral convergence lens 64a (see FIGS. 5A and 5B) at the termination end of the second linear accelerator 15b, adjusts the convergence and the divergence of the high-energy acceleration ion beam passing through the high-energy multi-stage linear acceleration unit 14, and causes the ion beam having an optimal two-dimensional beam profile to be incident to the beam deflection unit 16 of the rear stage.

In the direction of the electric field generated in the acceleration gap of the radio frequency linear accelerator, the ion acceleration direction and the ion deceleration direction change at every several tens of nano seconds. In order to accelerate the ion beam to the high energy, the electric field needs to be directed in the acceleration direction when the ions enter all acceleration gaps which exist at several tens of places. The ions that are accelerated by a certain acceleration gap need to pass through a space (a drift space) in which the electric field between two acceleration gaps is shielded until the electric field of the next acceleration gap is directed in the acceleration direction. Since the ions are decelerated even at the early timing or the late timing, the ions may not reach the high energy. Further, since it is a very strict condition that the ions are carried along the acceleration phase in all acceleration gaps, the ion beam that reaches the predetermined energy is a resultant obtained from a difficult selection for the mass, the energy, and the charge (factors for determining the velocity) by the radio frequency linear accelerator. In this meaning, the radio frequency linear accelerator is also a good velocity filter.

(Beam Deflection Unit)

As illustrated in FIG. 1, the beam deflection unit 16 includes the energy analysis electromagnet 24 as the energy filter deflection electromagnet (EFM), the energy width confining slit 27 (see FIGS. 5A and 5B), the energy analysis slit 28, the lateral convergence quadrupole lens 26 that controls the deflected energy dispersion, and the deflection electromagnet 30 that has an implantation angle correction function.

FIGS. 5A and 5B are top views illustrating a schematic configuration of the EFM (the energy analyzing deflection electromagnet), the energy width confining slit, the energy analysis slit, the BM (the lateral center orbit correcting deflection electromagnet), the beam shaper, and the beam scanner (the scanner). Furthermore, the sign L illustrated in FIG. 5A indicates the center orbit of the ion beam.

The ion beam that passes through the high-energy multi-stage linear acceleration unit 14 enables the energy distribution by a synchrotron vibration. Further, there is a case in which the beam having a center value slightly deviated from the predetermined energy may be emitted from the high-energy multi-stage linear acceleration unit 14 when the acceleration phase adjustment amount is large. Therefore, the magnetic field of the energy filter deflection magnet (EFM) is set so that only the ions having desired energy may pass by the beam deflection unit 16 to be described later, and a part of the beam selectively passes by the energy width confining slit 27 and the energy analysis slit 28, so that the ion energy is adjusted to the setting value. The energy width of the passing ion beam may be set in advance by the horizontal opening widths of the energy width confining slit and the analysis slit. Only the ions passing through the energy analysis slit are led to the beamline of the rear stage, and are implanted into the wafer.

When the ion beam having the energy distribution is incident to the energy filter electromagnet (EFM) of which the magnetic field is controlled to a uniform value by the above-described feedback loop control system, the entire incident ion beam causes the energy dispersion while being deflected along the designed orbit, and the ions within a desired energy width range pass through the energy width confining slit 27 provided near the exit of the EFM. At the position, the energy dispersion increases to the maximum value, and the beam size $\sigma_1$ (the beam size in a case where the energy width does not exist) due to the emittance decreases to the minimum value. However, the beam width caused by the energy dispersion becomes larger than the beam width caused by the emittance. In a case where the ion beam in such a state is cut by the slit, the spatial distribution is cut sharply, but the energy distribution has a cut shape rounded by the energy width corresponding to $2\sigma_1$. In other words, for example, even when the slit width is set to the dimension corresponding to 3% of the energy width, a part of the ions having an energy difference with respect to the predetermined implantation energy smaller than 3% collide with the wall of the slit so as to disappear, but a part of the ions having an energy difference larger than 3% pass through the slit.

The energy analysis slit is installed at a position where the value of $\sigma_1$ becomes minimal. Since the value of $\sigma_1$ decreases to an ignorable value by the slit width at the position, the energy distribution is also cut sharply like the space distribution. For example, even in a case where the opening width of the energy analysis slit is also set to the dimension (0.03 η) corresponding to 3% of the energy width, all ions having an energy difference exceeding 3% and passing through the energy width confining slit are interrupted at the position. As a result, when the beam having a rectangular energy distribution at first passes through two slits, a dome-shaped distribution is formed in which the energy becomes a peak value at 0%, the height decreases by a half at ±3%, and the energy abruptly decreases to zero. Since the number of the ions having a small energy difference relatively increases, the energy width substantially decreases compared to the case where only one energy analysis slit is provided and the ion beam passes through the slit while having a substantially rectangular energy distribution.

In the double slit system, when the energy of the beam accelerated by the linac is slightly deviated from the predetermined implantation energy by the effect of cutting the end of the energy distribution, there is an effect that the energy deviation of the passed beam decrease. For example, in a case where the energy deviation is 3% when the energy width is ±3%, the plus side of the energy having the dome-shaped distribution in the energy distribution of the ion beam passing through the double slit becomes a half, and hence the energy center as the center of the distribution substantially becomes $\Delta E/E=1\%$. Meanwhile, when the ion beam is cut by the single energy analysis slit, the gravity center becomes $\Delta E/E=1.5\%$. The effect of rounding the distribution is essentially exhibited in a direction in which the deviation of the energy center is suppressed.

In this way, in order to improve the energy precision by decreasing both the energy width and the deviation of the energy center using the acceleration system having both the energy width and the energy deviation, the limitation of the energy using the double slit is effective.

Since the energy analysis electromagnet needs high magnetic field precision, highly precise measurement devices 86a and 86b for precisely measuring the magnetic field are provided (see FIG. 5B). The measurement devices 86a and 86b use the MRP to calibrate the hall probe and uses the hall probe to control the uniform magnetic field feedback control by the appropriate combination of the NMR (nuclear magnetic resonance) probe called the MRP (magnetic resonance probe) and the hall probe. Further, the energy analysis electromagnet is produced by strict precision so that the non-uniformity of the magnetic field becomes smaller than 0.01%. Further, each electromagnet is connected with a power supply having current setting precision and current stability of $1 \times 10^{-4}$ or more and a control device thereof.

Further, the quadrupole lens 26 as the lateral convergence lens is disposed between the energy analysis slit 28 and the energy analysis electromagnet 24 at the upstream side of the energy analysis slit 28. The quadrupole lens 26 may be formed in an electric field type or a magnetic field type. Accordingly, since the energy dispersion is suppressed after the ion beam is deflected in a U-shape and the beam size decreases, the beam may be transported with high efficiency. Further, since the conductance decreases at the magnetic pole portion of the deflection electromagnet, it is effective to dispose an outgas discharging vacuum pump in the vicinity of, for example, the energy analysis slit 28. In a case where a magnetically-elevated turbo molecular pump is used, the pump needs to be provided at a position where the pump is not influenced by the leakage magnetic field of the electromagnet of the energy analysis electromagnet 24 or the deflection electromagnet 30. By the vacuum pump, the beam current degradation due to the scattering of the remaining gas at the deflection unit is prevented.

When there is a large installation error in the quadrupole lens, the dispersion adjusting quadrupole lens 26, or the beam shaper 32 in the high-energy multi-stage linear acceleration unit 14, the center orbit of the beam illustrated in FIG. 5B is distorted, and the beam may easily disappear while contacting the slit. As a result, the final implantation angle and the final implantation position are also wrong. Here, the center orbit of the beam essentially passes through the center of the beam scanner 34 on the horizontal plane due to the magnetic field correction value of the deflection electromagnet 30 having an implantation angle correction function. Accordingly, the deviation of the implantation angle is corrected. Further, when an appropriate offset voltage is applied to the beam scanner 34, the distortion of the center orbit from the scanner to the wafer disappears, and hence the horizontal deviation of the implantation position is solved.

The ions that pass through the deflection electromagnets of the beam deflection unit 16 are subjected to a centrifugal force and a Lorentz force, and hence draws a circular-arc orbit by balance of these forces. When this balance is represented by a relation, a relation of $mv=qBr$ is established. Here, m indicates the mass of the ion, v indicates the velocity of the ion, q indicates the charge state of the ion, B indicates the magnetic flux density of the deflection electromagnet, and r indicates the curvature radius of the orbit. Only the ions in which the curvature radius r of the orbit matches the curvature radius of the magnetic center of the deflection electromagnet may pass through the deflection electromagnet. In other words, in a case where the ions have the same charge state, the ions that may pass through the deflection electromagnet applied with the uniform magnetic field B are only the ions having the specific momentum mv. The EFM is called the energy analysis electromagnet, but is actually a device that is used to analyze the momentum of the ion. The BM or the mass analysis electromagnet of the ion generation unit is the momentum filter.

Further, the beam deflection unit 16 may deflect the ion beam by 180° just by using a plurality of magnets. Accordingly, the high-energy ion implanter 100 in which the beamline has a U-shape may be realized by a simple configuration.

As illustrated in FIG. 5A, the beam deflection unit 16 deflects the ion beam emitted from the high-energy multi-stage linear acceleration unit 14 by 90° using the energy analysis electromagnet 24. Then, the beam path is further deflected by 90° using the deflection electromagnet 30 that is also used to correct the orbit, and is incident to the beam shaper 32 of the beam transportation line unit 18 to be described later. The beam shaper 32 shapes the incident beam and supplies the beam to the beam scanner 34. Further, the divergence of the beam due to the energy dispersion is prevented by the lens effect of the quadrupole lens 26 illustrated in FIG. 5B or an extreme decrease in the size of the beam is prevented by using the beam expansion effect based on the energy dispersion.

Figure 11A:
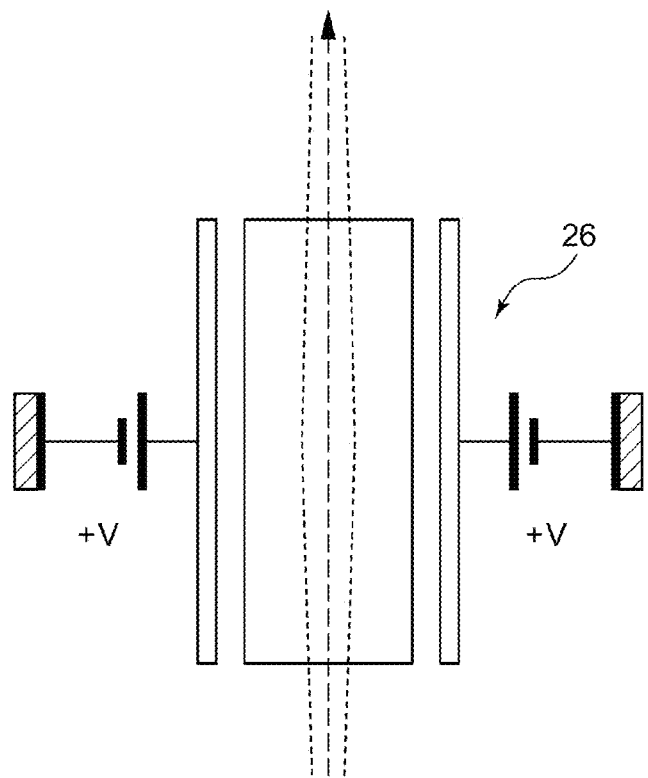
FIG. 11A is a schematic top view illustrating a quadrupole lens as a lateral convergence lens.
Figure 11B:
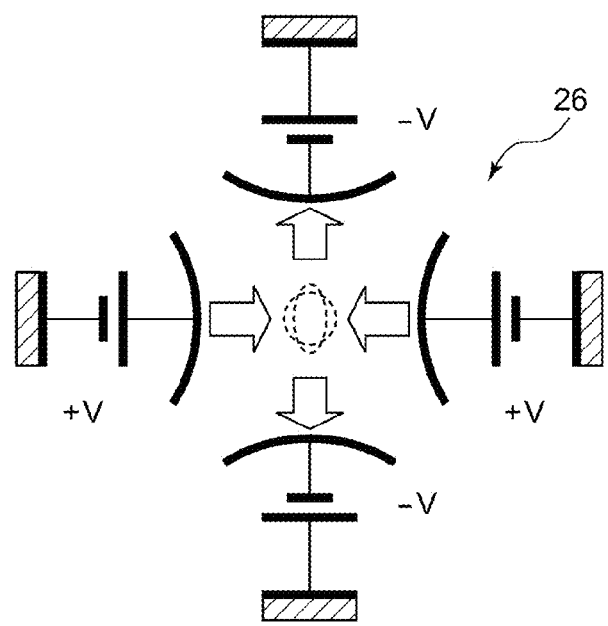
FIG. 11B is a schematic front view illustrating the quadrupole lens.

FIG. 11A is a schematic top view illustrating a quadrupole lens as a lateral convergence lens, and FIG. 11B is a schematic front view illustrating the quadrupole lens. The top view of FIG. 11A illustrates the electrode length in the beamline traveling direction of the quadrupole lens 26 and the effect in which the beam that diverges laterally with respect to the beam of the energy selected by the energy analysis electromagnet (the EFM deflection magnet) 24 converges laterally by the quadrupole lens 26. The front view of FIG. 11B illustrates the lateral convergence effect of the beam based on the convergence and divergence action of the electrode of the quadrupole lens 26.

As described above, the beam deflection unit 16 performs the deflection of the ion beam by 180° by a plurality of electromagnets between the high-energy multi-stage linear acceleration unit 14 and the beam transportation line unit 18 in the ion implanter that accelerates the ions generated from the ion source and transports the ions to the wafer so as to implant the ions thereto. That is, the energy analysis electromagnet 24 and the orbit correction deflection electromagnet 30 are respectively formed so as to have deflection angles of 90°. As a result, the total deflection angle becomes 180°. Furthermore, the amount of the deflection performed by one magnet is not limited to 90°, and may be the following combination.

(1) One magnet having deflection amount of 90°+two magnets having deflection amounts of 45°

(2) Three magnets having deflection amounts of 60°

(3) Four magnets having deflection amounts of 45°

(4) Six magnets having deflection amounts of 30°

(5) One magnet having deflection amount of 60°+one magnet having deflection amount of 120°

(6) One magnet having deflection amount of 30°+one magnet having deflection amount of 150°

The beam deflection unit 16 as the energy analysis unit is a folding path in the U-shaped beamline, and the curvature radius r of the deflection electromagnet forming the unit is an important parameter that limits the maximum energy of the beam to be transported and determines the entire width of the apparatus or the width of the center maintenance area (see FIGS. 5A and 5B). When the value is optimized, an increase in the entire width of the apparatus is suppressed without decreasing the maximum energy. Then, the gap between the high-energy multi-stage linear acceleration unit 14 and the beam transportation line unit 18 is widened, so that a sufficient work space R1 is ensured (see FIG. 1).

Figure 12A:
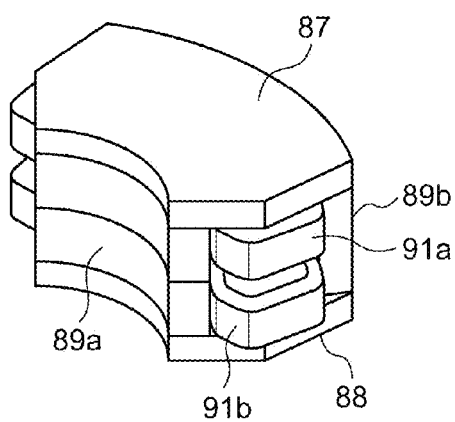
FIGS. 12A and 12B are perspective views illustrating an example of a configuration of an electromagnet.
Figure 12B:
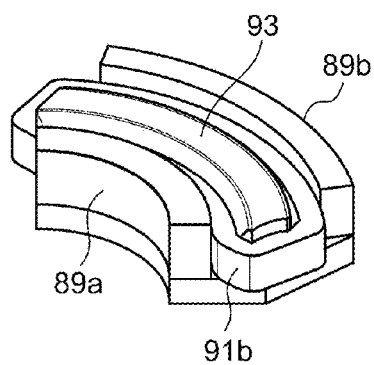
Figure 13:
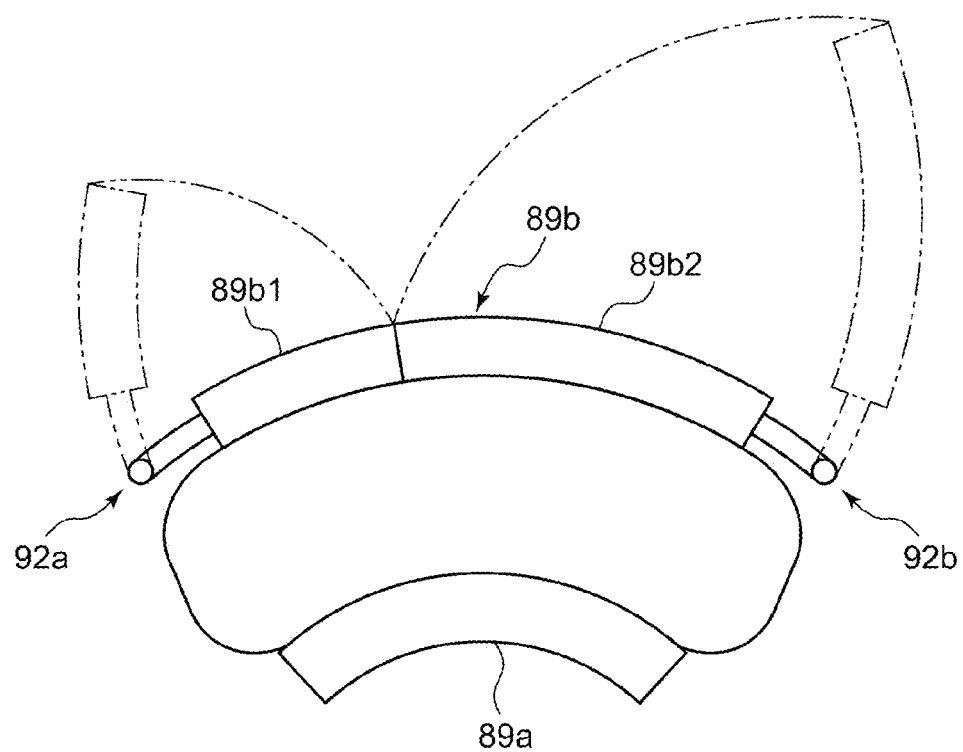
FIG. 13 is a schematic view illustrating an opening and closing portion included in the electromagnet.

FIGS. 12A and 12B are perspective views illustrating an example of a configuration of the electromagnet. FIG. 13 is a schematic view illustrating an opening and closing portion provided in the electromagnet. For example, as illustrated in FIGS. 12A and 12B, the electromagnet forming the energy analysis electromagnet 24 or the deflection electromagnet 30 includes an upper yoke 87, a lower yoke 88, inner and outer yokes 89a and 89b, an upper pole (not illustrated), a lower pole 93, an upper coil 91a, and a lower coil 91b. Further, as illustrated in FIG. 13, the outer yoke 89b is divided into two members 89b1 and 89b2, and the two members may be opened outward as folding double doors by opening and closing portions 92a and 92b. Then, a beam guide container (not illustrated) forming the beamline may be removably attached thereto.

Further, the vacuum container of the center portion of the beam deflection unit 16, for example, the container accommodating the energy width confining slit 27, the quadrupole lens 26, the energy analysis slit 28, and the like may be easily attached to and detached from the beamline. Accordingly, it is possible to simply enter and exit the work area of the center of the U-shaped beamline during the maintenance work.

The high-energy multi-stage linear acceleration unit 14 includes a plurality of linear accelerators that accelerate the ions. Each of the plurality of linear accelerators includes a common connection portion, and the connection portion may be removably attached to the energy analysis electromagnet 24 located at the upstream side in relation to the energy analysis slit 28 in the plurality of electromagnets. Similarly, the beam transportation line unit 18 may be removably attached to the deflection electromagnet 30.

Further, the energy analysis electromagnet 24 that is installed at the upstream side of the energy analysis slit 28 and includes the electromagnet may be formed so as to attached and detached or connected to the upstream high-energy multi-stage linear acceleration unit 14. Further, in a case where the beam transportation line unit 18 to be described later is configured as a module type beamline unit, the deflection electromagnet 30 that is installed at the downstream side of the energy analysis slit 28 may be attached and detached or connected to the downstream beam transportation line unit 18.

The linac and the beam deflection unit are respectively disposed on plane trestles, and are formed so that the ion beam orbit passing through the units are substantially included in one horizontal plane (the orbit after the deflection of the final energy filter is excluded).

(Beam Transportation Line Unit)

FIG. 6A is a top view illustrating a schematic configuration from the beam scanner to the substrate processing/supplying unit along the beamline after the beam collimator, and FIG. 6B is a side view illustrating a schematic configuration from the beam scanner to the substrate processing/supplying unit along the beamline after the beam collimator.

Only the necessary ion species are separated by the beam deflection unit 16, and the beam that is formed only by the ions having a necessary energy value is shaped in a desired cross-sectional shape by the beam shaper 32. As illustrated in FIGS. 5A to 6B, the beam shaper 32 is configured as (an electric field type or a magnetic field type) convergence/divergence lens group such as a Q (quadrupole) lens. The beam having a shaped cross-sectional shape is scanned in a direction parallel to the surface of FIG. 1A by the beam scanner 34. For example, the beam shaper is configured as a triplet Q lens group including a lateral convergence (longitudinal divergence) lens QF/a lateral divergence (a longitudinal convergence) lens QD/a lateral convergence (a longitudinal divergence) lens QF. If necessary, the beam shaper 32 may be configured by each of the lateral convergence lens QF and the lateral divergence lens QD or the combination thereof.

As illustrated in FIGS. 5A and 5B, the faraday cup 80b (called a resolver-faraday cup) for measuring the total beam current of the ion beam is disposed at a position directly before the beam shaper 32 of the foremost portion inside the scanner housing.

FIG. 14A is a schematic front view illustrating the resolver-faraday cup 80b, and FIG. 14B is a schematic view illustrating an operation of the resolver-faraday cup 80b.

The resolver-faraday cup 80b is formed so as to be extracted in the vertical direction on the beamline by a driving mechanism, and is formed so that the opening faces the upstream side of the beamline while having a rectangular square shape in the horizontal direction. The resolver-faraday cup is used to completely interrupt the ion beam that reaches the downstream side of the beamline if necessary other than the purpose of measuring the total beam current of the ion beam during the adjustment of the linac and the beam deflection portion. Further, the resolver-faraday cup 80b, the beam scanner 34, a suppression electrode 74, and ground electrodes 76a, 78a, and 78b are accommodated in a scanner housing 82.

The beam scanner 34 is a deflection scan device (called a beam scanner) that causes the ion beam to periodically scan the horizontal direction perpendicular to the ion beam traveling direction in a reciprocating manner by the periodically changing electric field.

The beam scanner 34 includes a pair of (two) counter scan electrodes (bipolar deflection scan electrodes) that are disposed so as to face each other with the ion beam passage region interposed therebetween in the beam traveling direction. Then, a scan voltage that changes to positive and negative values at a predetermined frequency in the range of 0.5 Hz to 4000 Hz and is approximated to the triangular wave is applied to two counter electrodes in the form of plus and minus values. The scan voltage generates a changing electric field that deflects the beam passing through the gap between two counter electrodes positive and negative inversely. Then, the beam that passes through the gap is scanned in the horizontal direction by the periodic change of the scan voltage.

The amount of the crystal damage generated inside the silicon wafer during the high-energy ion implantation is inverse proportional to the scan frequency. Then, there is a case in which the amount of the crystal damage influences the quality of the produced semiconductor device. In such a case, the quality of the produced semiconductor device may be improved by freely setting the scan frequency.

Further, an offset voltage (a fixed voltage) is superimposed on the scan voltage in order to correct the amount of the beam positional deviation measured directly near the wafer in a state where the scan voltage is not applied thereto. Accordingly, the scan range is not deviated in the horizontal direction due to the offset voltage, and hence the bilaterally symmetrical ion implantation may be performed.

The suppression electrode 74 that includes an opening in the ion beam passage region is disposed between two ground electrodes 78a and 78b at the downstream side of the beam scanner 34. The ground electrode 76a is disposed before the scan electrode at the upstream side thereof, but if necessary, the suppression electrode having the same configuration as that of the downstream side may be disposed. The suppression electrode suppresses the intrusion of electrons to the positive electrode.

Further, a ground shielding plate 89 is disposed at each of the upper and lower sides of deflection electrodes 87a and 87b. The ground shielding plate prevents the secondary electrons accompanied by the beam from flowing to the positive electrode of the beam scanner 34 from the outside. The power supply of the scanner is protected by the suppression electrode and the ground shielding plate, and hence the orbit of the ion beam is stabilized.

A beam parking function is provided at the rear side of the beam scanner 34. The beam parking function is formed so that the ion beam passing through the beam scanner is largely deflected in the horizontal direction if necessary so as to be led to the beam dump.

The beam parking function is a system that instantly stops the transportation of the beam within 10 μs in a case where an implantation error such as a dose uniformity error occurs when an unexpected problem such as a discharge of an electrode occurs during the ion implantation and an implantation operation is continued. In fact, at the moment in which the noticeable degradation in the beam current is detected, the output voltage of the beam scanner power supply is increased to 1.5 times the voltage corresponding to the maximum scan width, and the beam is led to the beam dump near the parallel lens. The beam irradiation position on the wafer at the moment in which the problem occurs is stored, and the beam is returned to the original orbit at the moment in which the wafer moves for the scanning operation in the vertical direction moves to the position after the problem is solved, thereby continuing the ion implantation as if no problem occurs.

A beam scan space portion is provided in a long section at the downstream side of the beam scanner 34 inside the scan housing, and hence a sufficient scan width may be obtained even when the beam scan angle is narrow. At the rear side of the scan housing located at the downstream side of the beam scan space portion, the deflected ion beam is adjusted to be directed to the direction of the ion beam before the beam is deflected. That is, the beam collimator 36 is installed which curves the beam so as to be parallel to the beamline.

Since the aberration (a difference in focal distance between the center portion of the beam collimator and left and right ends) generated in the beam collimator 36 is proportional to the square of the deflection angle of the beam scanner 34, the aberration of the beam collimator may be largely suppressed when the beam scan space portion is increased in length and the deflection angle is decreased. If the aberration is large, the center portion and the left and right ends have different beam sizes and beam divergence angles when the ion beam is implanted into the semiconductor wafer, and hence the quality of the product becomes non-uniform.

Further, when the length of the beam scan space portion is adjusted, the length of the beam transportation line unit may match the length of the high-energy multi-stage linear acceleration unit 14.

Figure 7:
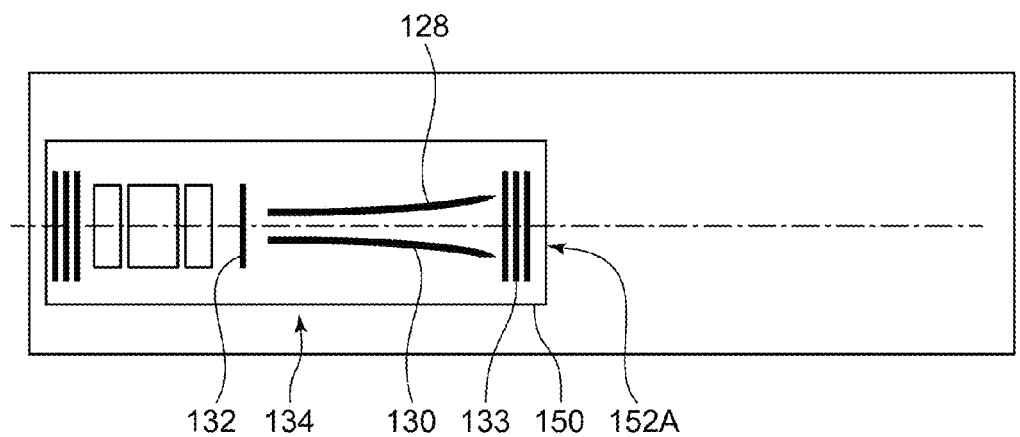
FIG. 7 is a schematic top view illustrating a main part of an example of the beam scanner.
Figure 8:
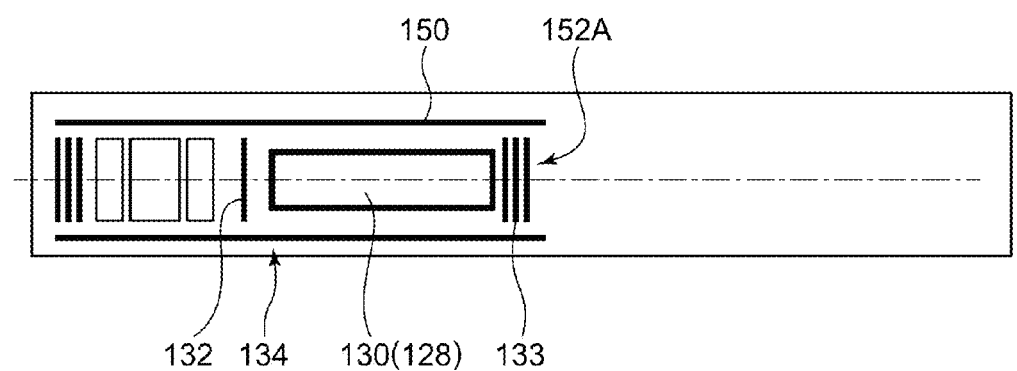
FIG. 8 is a schematic side view illustrating a main part of an example of the beam scanner.
Figure 9:
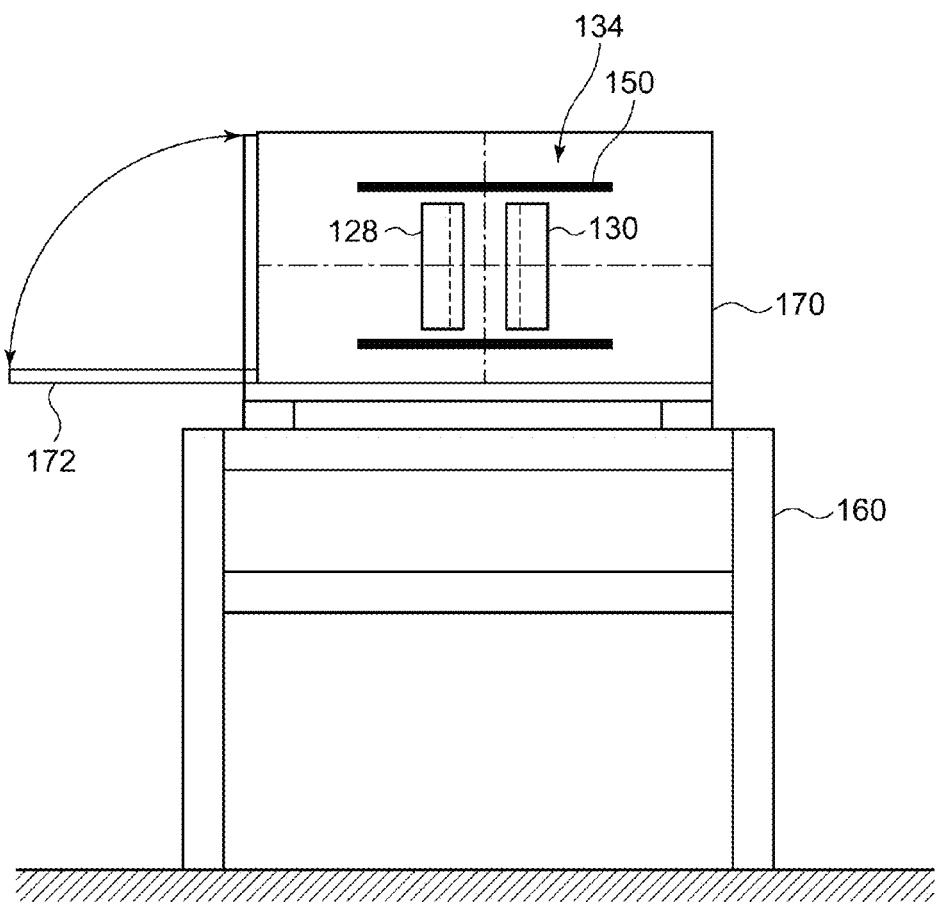
FIG. 9 is a schematic front view illustrating a structure in which an example of the beam scanner is removably attached to a halfway position of an ion beamline path when viewed from the downstream side.

FIG. 7 is a schematic top view illustrating a main part of an example of the beam scanner. FIG. 8 is a schematic side view illustrating a main part of an example of the beam scanner. FIG. 9 is a schematic front view illustrating a structure in which an example of the beam scanner is removably attached to the halfway position of the ion beamline when viewed from the downstream side.

As illustrated in FIGS. 7 and 8, in a beam scanner 134, a pair of deflection electrodes 128 and 130 and ground electrodes 132 and 133 assembled near the upstream and downstream sides thereof are accommodated and installed inside a box 150. An upstream opening (not illustrated) and an opening 152A larger than the opening of the ground electrode 133 are respectively provided at the positions corresponding to the openings of the ground electrodes 132 and 133 at the upstream side surface and the downstream side surface of the box 150.

The connection between the deflection electrode and the power supply is realized in the feed through structure. Meanwhile, the upper surface of the box 150 is provided with a terminal and a ground terminal used to connect the deflection electrodes 128 and 130 to the power supply. Further, a handle which is suitable for the attachment or the transportation is provided at each of side surfaces of the box 150 parallel to the beam axis. Furthermore, the box 150 is provided with a vacuum exhaust opening that decreases the pressure inside the beam scanner 134, and the vacuum exhaust opening is connected to a vacuum pump (not illustrated).

As illustrated in FIG. 9, the box 150 is slidably provided in a beam guide box 170 fixed onto a trestle 160. The beam guide box 170 is sufficiently larger than the box 150, and the bottom portion thereof is provided with two guide rails for sliding the box 150. The guide rail extends in a direction perpendicular to the beam axis, and the side surface of the beam guide box 170 of one end side thereof may be opened and closed by a door 172. Accordingly, the box 150 may be simply extracted from the beam guide box 170 during the repair and the check of the beam scanner 134. Furthermore, in order to lock the box 150 press-inserted into the beam guide box 170, the other end of the guide rail is provided with a locking mechanism (not illustrated).

The scanner peripheral unit members are work targets during the maintenance of the beamline, and the maintenance work may be easily performed from the work space R1. Similarly, the maintenance work of the high-energy multi-stage linear acceleration unit 14 may be easily performed from the work space R1.

The beam collimator 36 is provided with an electric field collimating lens 84. As illustrated in FIGS. 6A and 6B, the electric field collimating lens 84 includes a plurality of acceleration electrode sets and a plurality of deceleration electrode sets substantially having a hyperbolic shape. Each of the pair of electrodes faces each other with an acceleration-deceleration gap interposed therebetween and having a width not causing a discharge, and the acceleration-deceleration gap forms an electric field that is strengthened in proportional to a distance between the reference axis and the axial element causing the acceleration or deceleration velocity of the ion beam and having an element of influencing the lateral convergence of the ion beam.

The downstream electrode in the pair of electrodes with the acceleration gap interposed therebetween and the upstream electrode of the deceleration gap are formed as an integrated structure and the downstream electrode of the deceleration gap and the upstream electrode of the next acceleration gap are formed as an integrated structure so as to have the same potential. As illustrated in FIG. 6B, each of the structures includes an upper unit and a lower unit, and a space portion through which the ion beam passes is formed between the upper unit and the lower unit.

From the upstream side of the electric field collimating lens 84, the first electrode (the incident electrode) and the final electrode (the emission electrode) are maintained at the ground potential. Accordingly, the energy of the beam at the positions before and behind the collimating lens 84 does not change.

In the intermediate electrode structure, the exit electrode of the acceleration gap and the entrance electrode of the deceleration gap are connected with a negative power supply 90 having a variable constant voltage, and the exit electrode of the deceleration gap and the entrance electrode of the acceleration gap are connected with a positive power supply having a variable constant voltage (at the n-stage, negative, positive, negative, positive, negative, and the like). Accordingly, the ion beam is gradually directed toward the direction parallel to the center orbit of the beamline while being accelerated and decelerated repeatedly. Finally, the ion beam reaches the orbit parallel to the ion beam traveling direction (the beamline orbit direction) before the deflection scanning operation.

In this way, the beam that is scanned by the beam scanner 34 becomes parallel to the axis (the reference axis) of the deflection angle 0° parallel to the ion beam traveling direction (the beamline orbit direction) before the scan operation by the beam collimator 36 including the electric field collimating lens and the like. At this time, the scan region is formed so as to be bilaterally symmetrical to each other with respect to the reference axis.

The ion beam that is emitted from the electric field collimating lens 84 is sent to the electric field final energy filter 38 (AEF (94): Angular Energy Filter). In the final energy filter 94, a final analysis is performed on the energy of the ion beam to be directly implanted into the wafer, only the ion species having a necessary energy value are selected, and the neutralized particles or the ions having a different ion charge state are removed. The final energy filter 94 of the electric field deflection is configured as a plate-shaped deflection electrode including a pair of plane or curved surfaces facing each other in the vertical direction of the beamline orbit direction, is curved downward by the deflection action of the final energy filter 94 in the vertical direction of the beamline orbit direction, and is curved so as to match the ion beam orbit.

As illustrated in FIGS. 6A and 6B, the electric field deflection electrode is configured as a pair of AEF electrodes 104, and is disposed so that the ion beam is interposed from the vertical direction. In the pair of AEF electrodes 104, a positive voltage is applied to the upper AEF electrode 104, and a negative voltage is applied to the lower AEF electrode 104. During the deflection by the electric field, the ion beam is deflected downward by about 10 to 20° by the action of the electric field generated between the pair of AEF electrodes 104, and hence only the ion beam having target energy is selected. As illustrated in FIG. 6B, only the ion beam having a charge state selected in the final energy filter 94 is deflected downward at the set orbit angle. The beam that is formed by only the ions selected in this way is uniformly irradiated to the wafer 200 as the irradiation target at an accurate angle.

Figure 10:
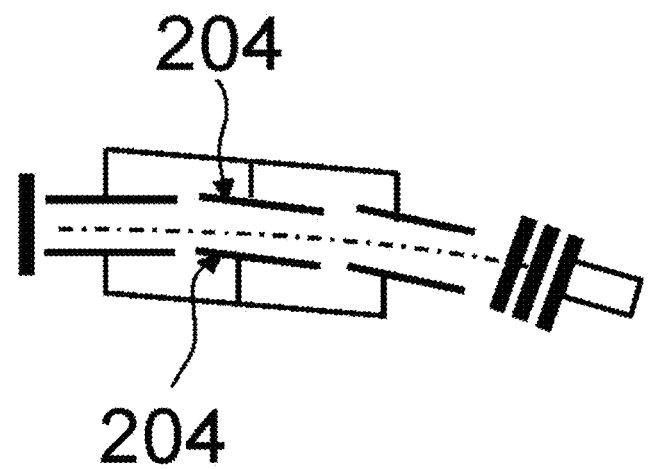
FIG. 10 is a schematic view illustrating another aspect of a deflection electrode of an angle energy filter.

In a case where the high-energy beam is actually deflected, a pair of plate-shaped deflection electrodes 204 facing each other in the vertical direction is divided into n number of segments in the longitudinal direction in accordance with the deflection angle and the curvature radius when the deflection electrodes are curved so as to match the ion beam orbit as illustrated in FIG. 10. Thus, the production precision or the economic efficiency is excellent in the plate-shaped electrode of which the upper electrode and the lower electrode are maintained at the same potential. Further, the plate-shaped deflection electrode that is divided into n number of segments in the longitudinal direction may be formed as n number of upper and lower plate-shaped electrodes set to different potentials other than the configuration in which the upper electrode and the lower electrode are maintained at the same potential.

With such a structure, the electric field type energy filter may be mounted on the high-energy scan beam transportation line. Since the beam is deflected in a direction perpendicular to the beam scan surface by the electric field, the energy analysis may be performed without influencing the implantation ion density distribution (the uniformity) in the beam scan direction.

Further, in addition to the mounted final energy filter, the beamline is equipped with three kinds of beam filters, that is, the radio frequency linear accelerator of the high-energy multi-stage linear acceleration unit 14, the magnetic field type EFM (the energy analysis electromagnet 24) and the BM (the deflection electromagnet 30) of the U-shaped deflection portion, and the final energy filter. As described above, the radio frequency linear accelerator is the velocity (v) filter, the EFM and the BM are the momentum (mv) filters, and the final energy filter is the energy ($mv^2/2$) filter as its name. In this way, when the different triple filters are used, a very pure ion beam that has high energy purity compared to the related art and has a small amount of particles or metal contamination may be supplied to the wafer.

Furthermore, in function, the EFM removes the energy contamination sneaking through the radio frequency linear accelerator or limits the energy width with high resolution, and the AEF mainly removes the ions subjected to a change in charge state by the resist outgas by the beam transportation line unit after the energy analysis using the EFM with comparatively low resolution.

The final energy filter 94 includes a ground electrode 108 that is provided at the upstream side of the final energy filter 94 and an electrode set provided with an AEF suppression electrode 110 provided between two ground electrodes at the downstream side. The AEF suppression electrode 110 suppresses the intrusion of the electrons to the positive electrode.

Dose cups 122 that are disposed at the left and right ends of the most downstream ground electrode of the final energy filter 94 measure the amount of the beam current to be implanted based on the dose amount.

(Substrate Processing/Supplying Unit)

In FIG. 6A, the arrow near the wafer 200 indicates the beam scanned in the arrow direction. Then, in FIG. 6B, the arrow near the wafer 200 indicates the reciprocation movement, that is, the mechanical scanning operation of the wafer 200 in the arrow direction. That is, when the beam is scanned in a reciprocating manner in, for example, one axial direction, the wafer 200 is driven by a driving mechanism (not illustrated) so that the wafer moves in a reciprocating manner in a direction perpendicular to the one axial direction.

The substrate processing/supplying unit 20 that supplies the wafer 200 to a predetermined position and performs an ion implantation thereon is accommodated in a process chamber (an implantation process chamber) 116. The process chamber 116 communicates with an AEF chamber 102. An energy defining slit (EDS) 118 is disposed inside the process chamber 116. The energy defining slit 118 is formed as a slit that is laterally long in the scan direction in order to separate only the ion beam having a meaningful energy value and a meaningful charge state and passing through the AEF by limiting the passage of the ion beam having a non-meaningful energy value and a non-meaningful charge state. Further, the energy defining slit 118 forms a slit body by a movable member in the vertical direction so as to adjust the separation gap of the slit, and may be used for various measurement purposes such as an energy analysis or an implantation angle measurement. Further, the movable upper and lower change slit members include a plurality of slit surfaces, and the slit width may be changed to a desired slit width in a manner such that the slit surfaces are changed and the axes of the upper and lower slits are adjusted or rotated in the vertical direction. A configuration may be also employed which decreases the cross contamination by sequentially changing the plurality of slit surfaces in response to the ion type.

A plasma shower 120 supplies low-energy electrons to the entire surface of the wafer 200 and the ion beam on the orbit in response to the beam current amount of the ion beam, and suppresses the charge-up of the positive charge generated in the ion implantation. Furthermore, a dose cup (not illustrated) that measures the dose amount may be disposed at each of left and right ends of the plasma shower 120 instead of the dose cups 122 disposed at the left and right ends of the most downstream ground electrode of the final energy filter 94.

A beam profiler 124 includes a beam profiler cup (not illustrated) that measures the beam current at the ion implantation position. The beam profiler 124 measures the ion beam density at the ion implantation position in the beam scan range while moving in the horizontal direction before the ion implantation. In a case where the predicted non-uniformity (PNU) of the ion beam does not satisfy the request of the process as a result of the beam profile measurement, the PNU is automatically adjusted to satisfy the process condition by correcting the control function of the application voltage of the beam scanner 34. Further, a configuration may be also employed in which a vertical profile cup (not illustrated) is provided in parallel to the beam profiler 124, the beam shape and the beam X-Y position are measured, the beam shape at the implantation position is checked, and the implantation angle or the beam divergence angle is checked by the combination of the beam width, the beam center position, and the divergence mask.

Figure 15:
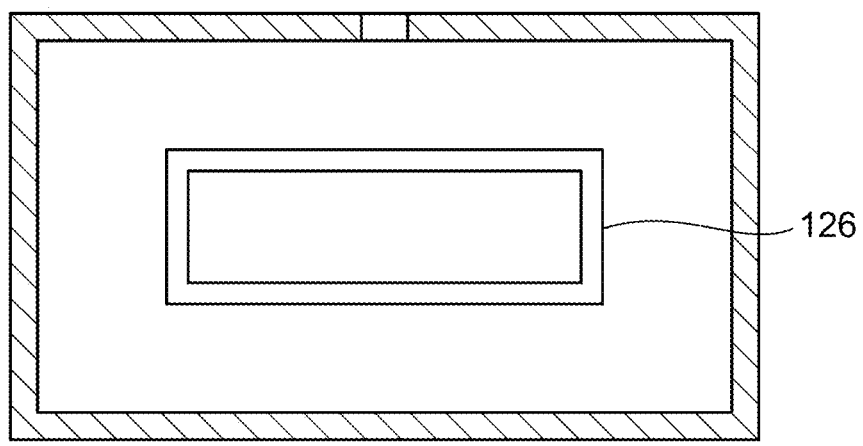
FIG. 15 is a schematic front view illustrating a lateral elongated faraday cup.

A lateral elongated faraday cup 126 with a beam current measurement function capable of measuring the ion beam in the scan range in the wafer region is disposed at the most downstream side of the beamline, and is configured to measure the final setup beam. FIG. 15 is a schematic front view illustrating the lateral elongated faraday cup. Furthermore, in order to reduce the cross contamination, the lateral elongated faraday cup 126 may include a changeable bottom surface of a faraday cup of a tripe surface structure capable of changing three surfaces of a triangular prism in response to the ion type. Further, a configuration may be also employed in which a vertical profile cup (not illustrated) is provided in parallel to the lateral elongated faraday cup 126, the beam shape or the vertical beam position is measured, and the implantation angle or the beam divergence angle in the vertical direction at the implantation position is monitored.

As described above, the high-energy ion implanter 100 is formed so that the units are disposed in a U-shape so as to surround the work space R1 as illustrated in FIG. 1. For this reason, a worker in the work space R1 may perform the replacement, the maintenance, and the adjustment of the parts of many units.

(Consideration of Entire Layout, Maintenance Workability, Manufacturability, and Global Environment)

The high-energy ion implanter 100 according to the embodiment accelerates the ion beam generated in the ion beam generation unit 12 by the high-energy multi-stage linear acceleration unit 14, changes the direction of the ion beam by the beam deflection unit 16, and irradiates the ion beam to the substrate existing in the substrate processing/supplying unit 20 provided at the termination end of the beam transportation line unit 18.

Further, the high-energy ion implanter 100 includes the high-energy multi-stage linear acceleration unit 14 and the beam transportation line unit 18 as the plurality of units. Then, the high-energy multi-stage linear acceleration unit 14 and the beam transportation line unit 18 are disposed so as to face each other with the work space R1 illustrated in FIG. 1 interposed therebetween. Accordingly, since the high-energy multi-stage linear acceleration unit 14 and the beam transportation line unit 18 disposed substantially linearly in the apparatus of the related art are disposed in a folded state, an increase in the entire length of the high-energy ion implanter 100 may be suppressed. Further, the curvature radiuses of the plurality of deflection electromagnets forming the beam deflection unit 16 are optimized so as to minimize the width of the apparatus. With such a configuration, the installation area of the apparatus is minimized, and the maintenance or the like of the high-energy multi-stage linear acceleration unit 14 or the beam transportation line unit 18 may be performed in the work space R1 interposed between the high-energy multi-stage linear acceleration unit 14 and the beam transportation line unit 18.

Further, the plurality of units constituting the high-energy ion implanter 100 includes the ion beam generation unit 12 that is provided at the upstream side of the beamline and generates the ion beam, the substrate processing/supplying unit 20 that is provided at the downstream side of the beamline and supplies the substrate so as to perform a process in which ions are implanted into the substrate, and the beam deflection unit 16 that is provided at the halfway position of the beamline from the ion beam generation unit 12 toward the substrate processing/supplying unit 20 and deflects the orbit of the ion beam. Then, the ion beam generation unit 12 and the substrate processing/supplying unit 20 are disposed at one side of the entire beamline, and the beam deflection unit 16 is disposed at the other side of the entire beamline. Accordingly, since the ion source 10 that needs to be subjected to the maintenance within a comparatively short time and the substrate processing/supplying unit 20 that needs to supply and acquire the substrate are disposed so as to be adjacent to each other, the movement area of the worker may be small.

Further, the high-energy multi-stage linear acceleration unit 14 includes a plurality of linear accelerators that accelerate the ions, and each of the plurality of linear accelerators may include a common connection portion. Accordingly, the number or the type of the linear accelerator may be easily changed in response to the energy necessary for the ions implanted into the substrate.

Further, the beam scanner 34 as the scanner device and the beam collimator 36 as the collimating lens device may include a standard-shaped connection portion with respect to the adjacent units. Accordingly, the number or the type of the linear accelerator may be easily changed. Then, the beam scanner 34 or the beam collimator 36 may be selected in response to the configuration and the number of the linear accelerator included in the high-energy multi-stage linear acceleration unit 14.

Further, in the high-energy ion implanter 100, the alignment (the positional adjustment) of the beam may be performed by integrating the vacuum chamber and the frame of each device and performing the assembly in accordance with the reference position of the vacuum chamber or the frame of the device. Accordingly, the troublesome alignment operation may be minimized, and the device set-up time may be shortened. Accordingly, the deviation of the axis caused by the mistake in work may be suppressed. Further, the alignment of the vacuum chambers may be performed by the unit of the module. Accordingly, the work load may be reduced. Further, the size of the modulated device may be decreased to be equal to or smaller than the size in which the device may easily move. Accordingly, the relocation load of the module or the high-energy ion implanter 100 may be reduced.

Further, the high-energy ion implanter 100 may be formed so that the high-energy multi-stage linear acceleration unit 14, the beam transportation line unit 18, the exhaust device, and the like are assembled to a single trestle. Further, the high-energy ion implanter 100 is formed so that the high-energy multi-stage linear acceleration unit 14, the beam deflection unit 16, and the beam transportation line unit 18 are included in one plane on the plane base. Accordingly, since each block of the high-energy ion implanter 100 may be directly transported while the blocks are fixed onto one plane base, a deviation in adjustment hardly occurs, and hence an effort for re-adjusting the blocks on site may be reduced. For this reason, it is possible to prevent an uneconomical problem in which many experts are sent to the installation site for a long period of time.

Further, when the plane base is formed in the middle portion of the trestle instead of the floor thereof, only the devices directly involved with the ion beam orbit may be mounted onto the plane base. Then, when a component such as a radio frequency cubic circuit as an auxiliary device may be assembled in the space formed below the plane base, the space utilization efficiency may be improved, and hence the ion implanter having a compactor size may be realized.

Thus, the high-energy ion implanter 100 may be also installed in a site where a sufficient installation place is not ensured, and may be used in a manner such that the high-energy ion implanter is transported to a demanded place in a state where the apparatus is assembled and adjusted inside a production factory, is fixed at the installation site, and is used by the final adjustment. Further, the high-energy ion implanter 100 may realize the high-energy ion implantation while satisfying the standard level of the semiconductor production line of the semiconductor production factory.

In this way, the high-energy ion implanter 100 may be decreased in size compared to the related art by examining the layout of the units or the devices, and hence may have an installation length that is about a half of the size of the related art. Further, the ion implanter according to the embodiment may be operated in a manner such that the components are assembled to the bases inside the production factory, are loaded in a transportation vehicle to be transported to the installation site while the ion beam orbit is established through the positional adjustment on the bases, are fixed to the trestles, and then the deviation in adjustment is finely adjusted to be removed. For this reason, the ion implanter may be remarkably easily and reliably adjusted on site by a person who is not an expert, and hence the set-up time may be shortened.

Further, when the layout like the elongated U-shaped folded beamline is employed, the ion implanter capable of highly precisely implanting the high-energy ions of 5 to 8 MeV in maximum may be realized. Further, the ion implanter includes a small installation area and a sufficient maintenance area by the layout having a center passage (a center region). Further, the power consumption may be decreased by the low-power consumption operation using the electric field parallel lens, the electric field type scanner, the electric field AEF, and the like during the operation of the ion implanter. In other words, the ion implanter according to the embodiment may perform the low-power consumption operation by employing the scan beam parallelization mechanism using the electric field deflection type collimating lens device.

While the invention has been described by referring to the above-described embodiment, the invention is not limited to the above-described embodiment, and the appropriate combination of the configurations of the embodiment or the substitution thereof is also included in the invention. Further, the combination of the embodiments or the process sequence thereof may be appropriately set or various modifications in design may be added to the embodiments based on the knowledge of the person skilled in the art. An embodiment having such modifications may be also included in the scope of the invention.

Hereinafter, another aspect of the invention will be described according to embodiments.

As illustrated in FIG. 1, the high-energy ion implanter 100 according to the embodiment is a high-energy ion implanter that accelerates an ion beam extracted from the ion source 10, transports the ion beam to the wafer along the beamline, and implants the ion beam into the wafer. The high-energy ion implanter 100 includes the ion beam generation unit 12 that includes the ion source 10 and the mass spectrometer 22, the high-energy multi-stage linear acceleration unit 14 that accelerates the ion beam so as to generate the high-energy ion beam, the high-energy beam deflection unit 16 that deflects the high-energy ion beam so as to analyze the energy and to change the direction of the ion beam toward the wafer, the beam transportation line unit 18 that transports the deflected high-energy ion beam to the wafer, and the substrate processing/supplying unit 20 that uniformly implants the transported high-energy ion beam into the semiconductor wafer. The beam transportation line unit 18 includes the beam shaper 32, the high-energy beam scanner 34, the high-energy beam collimator 36, and the high-energy final energy filter 38.

The high-energy ion implanter 100 scans the high-energy ion beam emitted from the beam deflection unit 16 at both sides of the reference trajectory of the beamline by the beam scanner 34, collimates the high-energy ion beam by the beam collimator 36, removes mixed ions which are different in any one of the mass, the ion charge state, and the energy by the high-energy final energy filter 38, and implants the resultant ions into the wafer. Further, the high-energy beam collimator 36 is an electric field type beam collimator that collimates the scan beam while performing (repeating) the acceleration and the deceleration of the high-energy beam by the electric field.

Further, as illustrated in FIGS. 6A and 6B, the beam collimator 36 includes at least a pair of acceleration electrodes 135 (135b and 135c) which has an opening 135a corresponding to the beamline L1 and faces each other with a gap G1 so as to generate an electric field for accelerating the ions in the beam traveling direction and at least a pair of deceleration electrodes 136 (136b and 136c) which has an opening 136a corresponding to the beamline L1 and faces each other with a gap G2 so as to generate an electric field for decelerating the ions in the beam traveling direction.

The pair of acceleration electrodes 135 accelerates the ion beam and deflects the ion beam toward the reference trajectory. Further, the pair of deceleration electrodes 136 decelerates the ion beam and deflects the ion beam toward the reference trajectory.

Each of the pair of acceleration electrodes 135 and the pair of deceleration electrodes 136 includes two electrodes that face each other with a gap therebetween so as to generate an electric field serving as an element for accelerating or decelerating the high-energy ion beam and an element for deflecting the high-energy ion beam. Then, the acceleration gap exit side electrode 135c and the deceleration gap entrance side electrode 136b have the same potential and the deceleration gap exit side electrode 136c and the acceleration gap entrance side electrode 135b have the same potential. Further, these electrodes are integrally formed.

According to this aspect, the scanned high-energy ion beam may be collimated in a bilaterally symmetric state, and hence the highly precise ion implantation may be performed.

Further, in the beam collimator 36 illustrated in FIGS. 6A and 6B, the potential of the upstream electrode 135b of the beamline in the pair of acceleration electrodes 135 is set to a ground potential, the downstream electrode 135c of the beamline in the pair of acceleration electrodes 135 and the upstream electrode 136b of the beamline in the pair of deceleration electrodes 136 are electrically connected (integrated) so as to have a potential of −50 kV by the parallelization power supply 90, and the potential of the downstream electrode 136c of the beamline of the pair of deceleration electrodes 136 is set to a ground potential.

In a case where the ion beam is collimated by the electric field generated by the beam collimator 36 with such a configuration, the ion beam is accelerated or decelerated between the electrodes so that the ion energy also changes. However, since the potentials of the entrance and the exit of the beam collimator 36 are equal to each other, a change in energy does not occur as a whole. That is, the beam collimator 36 is formed so that the energy of the ion beam scanned by the beam scanner 34 is equal to the energy of the ion beam collimated by the acceleration electrode 135 and the deceleration electrode 136.

Figure 16:
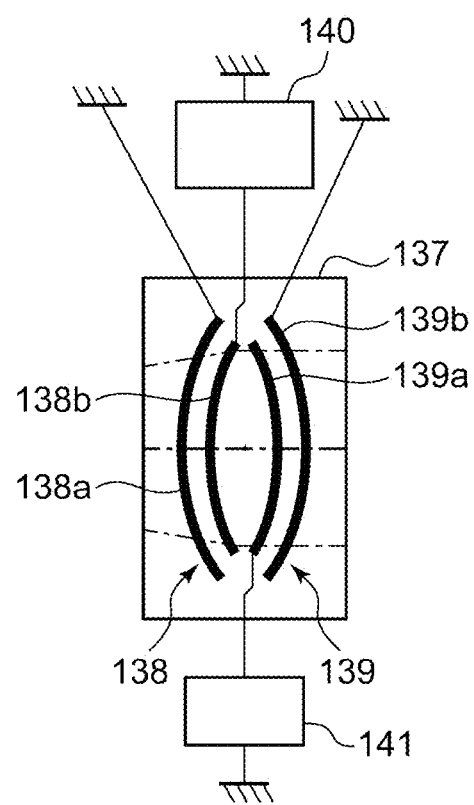
FIG. 16 is a top view illustrating a schematic configuration of a beam collimator as an aspect of the embodiment.

FIG. 16 is a top view illustrating a schematic configuration of the beam collimator according to the aspect of the embodiment. Furthermore, the same reference numerals will be given to the same components as those of the beam collimator 36 illustrated in FIGS. 6A and 6B, and the description thereof will not be appropriately repeated.

In the beam collimator 137 illustrated in FIG. 16, the potential of the upstream electrode 138a of the beamline in the pair of acceleration electrodes 138 is set to a ground potential, the first potential of the downstream electrode 138b of the beamline in the pair of acceleration electrodes 138 is set to V1 [V] (V1>0), the second potential of the upstream electrode 139a of the beamline in the pair of deceleration electrodes 139 is set to −V2 [V] (V2>0), and the potential of the downstream electrode 139b of the beamline in the pair of deceleration electrodes 139 is set to a ground potential. The electrode 138a is connected with a parallelization power supply 140 that applies a positive voltage, and the electrode 139a is connected with a parallelization power supply 141 that applies a negative voltage.

Furthermore, a configuration may be employed in which a negative voltage is applied to the parallelization power supply 140 and a positive voltage is applied to the parallelization power supply 141. Further, the first potential and the second potential may be formed so as to satisfy the relation of |V1|=|V2|. Accordingly, the ion beam may be collimated while being accelerated and decelerated with a balance. Further, the parallelization power supply 140 and the parallelization power supply 141 may be configured as the power supplies having the same configuration.

Figure 17A:
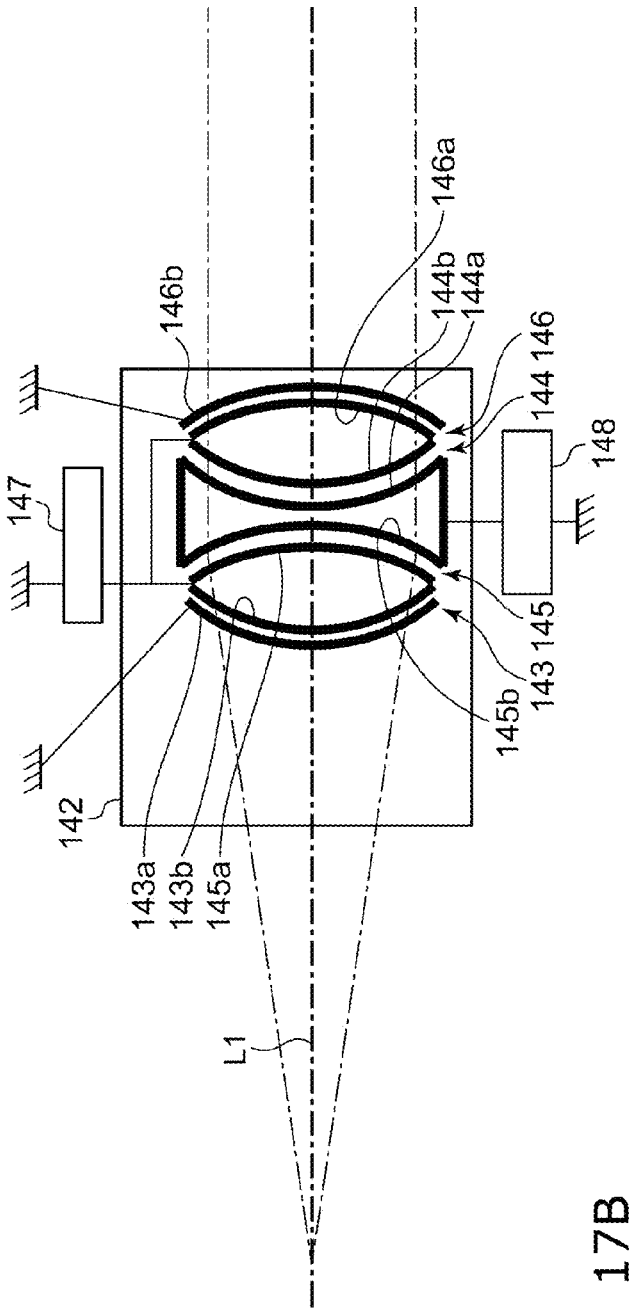
FIG. 17A is a top view illustrating a schematic configuration of a beam collimator as an aspect of the embodiment.
Figure 17B:
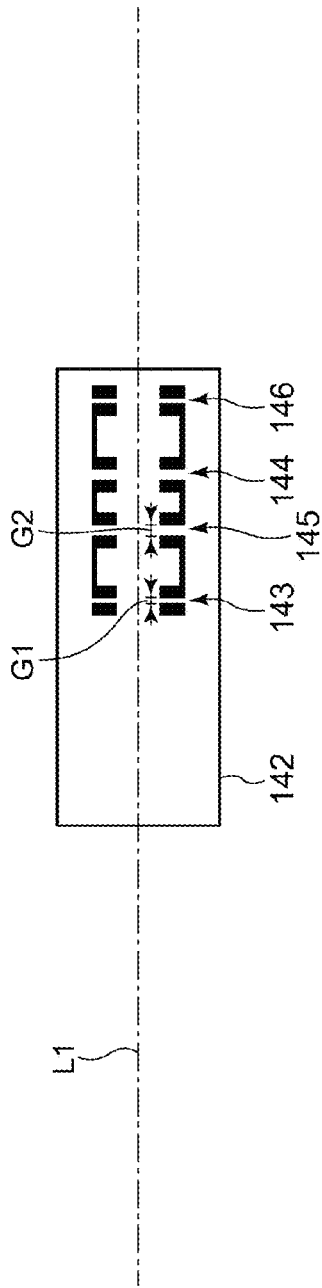
FIG. 17B is a side view illustrating a schematic configuration of the beam collimator as the aspect of the embodiment.

FIG. 17A is a top view illustrating a schematic configuration of the beam collimator according to the aspect of the embodiment, and FIG. 17B is a side view illustrating a schematic configuration of the beam collimator according to the aspect of the embodiment. Furthermore, the same reference numerals will be given to the same components as those of the beam collimator 36 illustrated in FIGS. 6A and 6B, and the description thereof will not be appropriately repeated.

The beam collimator 142 illustrated in FIGS. 17A and 17B is configured as an acceleration-deceleration electrode lens group that includes multiple pairs of acceleration electrodes 143 and 144 and multiple pairs of deceleration electrodes 145 and 146, and is configured to gradually collimate the scanned ion beam. Accordingly, since the voltage applied to one acceleration electrode or one deceleration electrode may be decreased, the power supply may be simplified and decreased in size. Further, the occurrence of the discharge may be also suppressed.

Further, a downstream electrode 143b of the acceleration electrode 143 and an upstream electrode 145a of the deceleration electrode 145 are electrically connected to each other so as to have the same potential, and are connected to a first parallelization power supply 147. Further, a downstream electrode 145b of the deceleration electrode 145 and an upstream electrode 144a of the acceleration electrode 144 are electrically connected to each other so as to have the same potential, and are connected to a second parallelization power supply 148. Further, the downstream electrode 144b of the acceleration electrode 144 and an upstream electrode 146a of the deceleration electrode 146 are electrically connected to each other so as to have the same potential, and are connected to the first parallelization power supply 147. Furthermore, an upstream electrode 143a of the acceleration electrode 143 and a downstream electrode 146b of the deceleration electrode 146 are set to a ground potential. In this way, when the voltages applied to a part of the electrodes are set to the same voltage, the number of the power supplies in use may be decreased.

Furthermore, among the multiple pairs of acceleration electrodes 143 and 144 and the multiple pairs of deceleration electrodes 145 and 146, the electrode 143a as the entrance ground electrode disposed at the most upstream side of the beamline and the electrode 143b adjacent to the electrode 143a may forma first suppression electrode that suppresses the inflow of electrons, and the electrode 146b as the exit ground electrode disposed at the most downstream side of the beamline and the electrode 146a adjacent to the electrode 146b may form a second suppression electrode that suppresses the inflow of electrons. Accordingly, there is no need to separately provide the suppression electrode.

Further, when the voltage applied to the downstream electrode 143b of the acceleration electrode 143 by the first parallelization power supply 147 is indicated by −V1 [V] (V1>0), the voltage applied to the downstream electrode 145b of the deceleration electrode 145 by the second parallelization power supply 148 is indicated by V2[V] (V2>0), the gap between two electrodes 143a and 143b of the acceleration electrode 143 is indicated by G1, and the gap between two electrodes 145a and 145b of the deceleration electrode 145 is indicated by G2, the following relation may be satisfied.

$$|V1|/G1=|V1+V2|/G2$$

In this way, when the electric field strength between the electrodes in the acceleration electrode and the deceleration electrode becomes uniform, the ion beam may be collimated while being accelerated and decelerated with a balance.

Further, the beam collimator 142 is formed so that the energy of the ion beam to be directly incident to the beam collimator is equal to the energy of the ion beam directly emitted from the beam collimator. More specifically, in the beam collimator 142, the incident electrode (143a) and the emission electrode (146b) of the beam collimator 142 are both grounded so that the energy of the ion beam scanned by the beam scanner is equal to the energy of the ion beam collimated by the pair of acceleration electrodes (143 and 144) and the pair of deceleration electrodes (145 and 146), the exit side electrode (143b and 144b) of the acceleration gap and the entrance side electrode (145a and 146a) of the deceleration gap are set to the same positive or negative potential, and the deceleration gap exit side electrode 145b and the acceleration gap entrance side electrode 144a are set to the same positive or negative potential.

Further, in the beam collimator 142, the electrode potentials are set so that the ion beam scanned at both sides of the reference trajectory by the beam scanner on the beamline toward the reference trajectory by the electric field generated by the pair of electrodes on the scan plane are deflected so as to match the orbit parallel to the reference trajectory.

Figure 18:
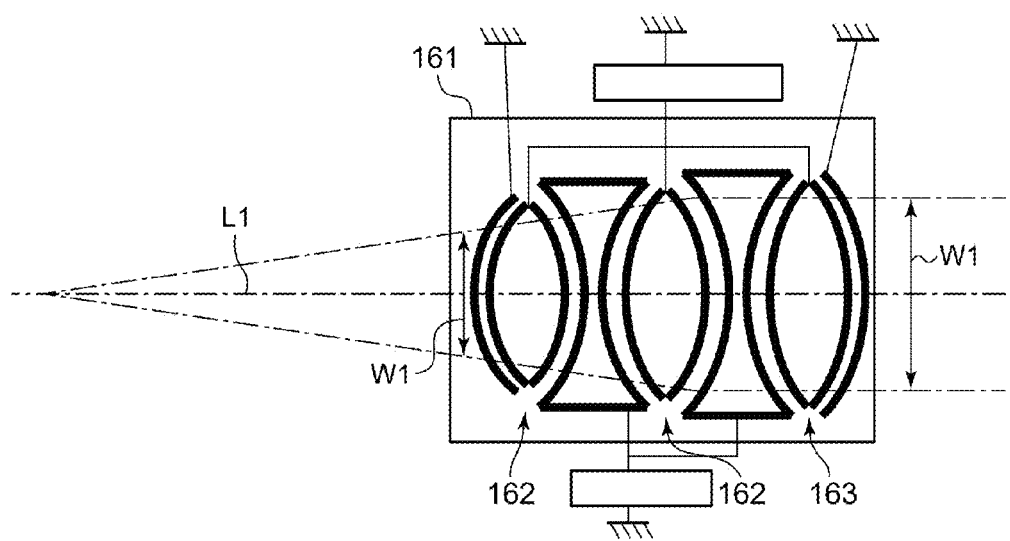
FIG. 18 is a top view illustrating a schematic configuration of a beam collimator according to a modified example of the embodiment.

FIG. 18 is a top view illustrating a schematic configuration of a beam collimator according to a modified example of the embodiment. A beam collimator 161 illustrated in FIG. 18 is provided with three collimating lenses 162, 163, and 164 formed by an acceleration electrode and a deceleration electrode. The ion beam that is deflected and scanned by the beam scanner is widened toward the downstream side of the beamline L1. Therefore, each of three collimating lenses 162, 163, and 164 is formed so that the width thereof gradually increases from the upstream side toward the downstream side of the beamline L1. Accordingly, the upstream collimating lens may be decreased in size.

Furthermore, the beam collimator 161 may be formed so that the width W1 of the collimated ion beam in the scan direction is two times or more the width W2 when the ion beam scanned by the beam scanner is incident to the beam collimator 161. Accordingly, the distance from the beam scanner to the beam collimator may be decreased.

The beam collimator according to the embodiment is formed by a pair of bow-shaped gap electrodes like the acceleration electrode or the deceleration electrode illustrated in FIGS. 6A and 6B and FIGS. 16 to 18. Further, the downstream electrode in the beamline of the pair of acceleration electrodes and the upstream electrode in the beamline of the pair of deceleration electrodes are configured as an electrode unit which is continuously integrated while both ends thereof are connected. Further, in the above-described beam collimator, the incident electrode and the emission electrode have a ground potential. However, when one of the incident electrode and the emission electrode is set to a ground potential and the other thereof is set to a specific potential or both electrodes are set to different specific potentials, it is possible to change the energy of the ion beam emitted after the beam incident to the beam collimator is collimated.

In this way, the high-energy ion implanter according to the embodiment may be operated at a low voltage while keeping the uniformity of the beam current density of the high-energy ion beam, and may obtain an electric field that does not change the beam energy before and after the beam passes through the beam collimator.

Further, the high-energy ion implanter according to the embodiment is configured to collimate the beam by causing the high-energy ion beam to pass through the elongated electric field. Then, the high-energy ion implanter is configured so that the beam is collimated by a plurality of electrode lens groups capable of accelerating and decelerating the ion beam and the acceleration-deceleration electrode lens group is configured as a pair of bow-shaped gap electrodes lenses, thereby preventing a change in beam energy before and after the ion beam passes therethrough.

Accordingly, the control of the parallelization power supply and the adjustment of the parallelization electric field may be easily performed, and the precision of the parallelization and the angle precision of the collimated beam in the beam traveling direction may be made satisfactory. Further, since a difference in beam path in the horizontal (scan) direction is symmetric, the beamline may be uniform in the horizontal direction, and hence the convergence and divergence uniformity of the beam may be maintained in the high-energy ion beam. As a result, the precision of the parallelization and the angle precision of the collimated beam in the beam traveling direction may be made high. In addition, the density distribution (profile) of the high-energy ion beam and the beam size in the beam scan range may not be substantially changed, and hence the uniformity of the beam current density may be maintained.

Further, in the beam collimator according to the embodiment disposed at the downstream side of the beam scanner having a small beam scan deflection angle and a beam scan width set as small as possible, the incident beam having a narrow beam scan width may be also gently collimated with high precision to the width in which the wafer may be scanned. As a result, a change in the quality of the beam decreases, and hence the uniformity of the beam current density may be maintained.

Furthermore, in a case where the acceleration-deceleration electrode lens group includes n pairs of acceleration electrodes and n pairs of deceleration electrodes and a first pair of acceleration electrodes, a first pair of deceleration electrodes, a second pair of acceleration electrodes, a second pair of deceleration electrodes, . . . , n-th (n is a natural number) pair of acceleration electrodes, and n-th pair of deceleration electrodes are disposed in this order along the beamline, the potentials may be set as below. Specifically, in the acceleration-deceleration electrode lens group, the first potential of the entrance electrode of the first pair of acceleration electrodes is set to a ground potential, the second potentials of the exit electrode of the first pair of acceleration electrodes and the entrance electrode of the first pair of deceleration electrodes are set to $-V1$ [V] ($V1>0$), the third potentials of the exit electrode of the first pair of deceleration electrodes and the entrance electrode of the second pair of acceleration electrodes are set to $V2$ [V] ($V2>0$), the fourth potentials of the exit electrode of the second pair of acceleration electrodes and the entrance electrode of the second pair of deceleration electrodes are set to $-V1$ [V] ($V1>0$), the fifth potentials of the exit electrode of the second pair of deceleration electrodes and the entrance electrode of the third pair of acceleration electrodes are set to $V2$ [V] ($V2>0$), and the $(2n+1)$-th potential of the exit electrode of the n-th pair of acceleration electrodes is set to the ground potential. Here, the second potential and the third potential may be set so as to satisfy the relation of $V1=V2$ or the relation of $V1 \neq V2$.

Furthermore, in a case where the acceleration-deceleration electrode lens group includes n pairs of acceleration electrodes and n pairs of deceleration electrodes and a first pair of acceleration electrodes, a first pair of deceleration electrodes, a second pair of acceleration electrodes, a second pair of deceleration electrodes, . . . , n-th (n is a natural number) pair of acceleration electrodes, and n-th pair of deceleration electrodes are disposed in this order along the beamline, the potentials may be set as below. Specifically, in the acceleration-deceleration electrode lens group, the first potential of the entrance side electrode of the first pair of acceleration electrodes is set to the inlet potential, the second potentials of the exit side electrode of the first pair of acceleration electrodes and the entrance side electrode of the first pair of deceleration electrodes are set to $-V1$ [V] ($V1>0$), the third potentials of the exit side electrode of the first pair of deceleration electrodes and the entrance side electrode of the second pair of acceleration electrodes are set to $V2$ [V] ($V2>0$), the fourth potentials of the exit side electrode of the second pair of acceleration electrodes and the entrance side electrode of the second pair of deceleration electrodes are set to $-V1$ [V] ($V1>0$), the fifth potentials of the exit side electrode of the second pair of deceleration electrodes and the entrance side electrode of the third pair of acceleration electrodes are set to V2 [V] (V2>0), and the (2n+1)-th potential of the exit side electrode of the n-th pair of acceleration electrodes is set to an outlet potential. Here, both of the inlet potential and the outlet potential are different from V1 or V2.

Furthermore, a configuration in which the arbitrary combination of the above-described components, or the component or the expression of the invention is substituted in the method, the device, and the system is valid as the aspect of the invention.

Priority is claimed to Japanese Patent Application No. 2013-112036, filed May 28, 2013, the entire content of which is incorporated herein by reference.

What is claimed is:

1. A high-energy ion implanter that accelerates an ion beam extracted from an ion source, transports the ion beam to a wafer along a beamline, and implants the ion beam into the wafer, the high-energy ion implanter comprising:
    a beam generation unit that includes an ion source and a mass analyzer;
    a high-energy multi-stage linear acceleration unit that accelerates the ion beam so as to generate a high-energy ion beam;
    a high-energy beam deflection unit that changes the direction of the high-energy ion beam toward the wafer;
    a beam transportation unit that transports the deflected high-energy ion beam to the wafer; and
    a substrate processing/supplying unit that uniformly implants the transported high-energy ion beam into a semiconductor wafer,
    wherein the beam transportation unit includes a beam shaper, a high-energy beam scanner, a high-energy beam collimator, and a high-energy final energy filter,
    wherein the high-energy ion beam emitted from the deflection unit is scanned at both sides of a reference trajectory of the beamline by the beam scanner and is collimated by the beam collimator, mixed ions which are different in any one of a mass, an ion charge state, and energy are removed by the high-energy final energy filter, and the resultant ions are implanted into the wafer, and
    wherein the high-energy beam collimator is an electric field type beam collimator that collimates a scan beam while performing the acceleration and the deceleration of the high-energy beam by an electric fields.

2. The high-energy ion implanter according to claim 1, wherein the electric field type beam collimator includes a pair of acceleration electrodes that accelerates the ion beam and deflects the ion beam toward the reference trajectory and a pair of deceleration electrodes that decelerates the ion beam and deflects the ion beam toward the reference trajectory, and is formed by an acceleration-deceleration electrode lens group including at least two sets or more of the pair of acceleration electrodes and the pair of deceleration electrodes.

3. The high-energy ion implanter according to claim 2, wherein the pair of acceleration electrodes or the pair of deceleration electrodes is a pair of electrodes as two electrodes that face each other with a gap therebetween so as to generate an electric field serving as an element for accelerating or decelerating the high-energy ion beam and an element for deflecting the high-energy ion beam, an exit side electrode of an acceleration gap and an entrance side electrode of a deceleration gap are set to the same potential, an exit side electrode of a deceleration gap and an entrance side electrode of an acceleration gap are set to the same potential, and each set of the same potential electrodes is integrally formed.

4. The high-energy ion implanter according to claim 2, wherein the electrode potentials are set so that the ion beam scanned at both sides of the reference trajectory by the beam scanner on the beamline is gradually deflected toward the reference trajectory by an electric fields generated by the pairs of electrodes on the scan plane so as to match the trajectory parallel to the reference trajectory.

5. The high-energy ion implanter according to claim 2, wherein at least one set of the pair of acceleration electrodes and the pair of deceleration electrodes included in the acceleration-deceleration electrode lens group are disposed in order of the pair of acceleration electrodes and the pair of deceleration electrodes from the upstream side of the beamline.

6. The high-energy ion implanter according to claim 2, wherein at least one set of the pair of acceleration electrodes and the pair of deceleration electrodes included in the acceleration-deceleration electrode lens group are disposed in order of the pair of deceleration electrodes and the pair of acceleration electrodes from the upstream side of the beamline,
    wherein a first suppression electrode is provided at the upstream side of the pair of deceleration electrodes, and
    wherein a second suppression electrode is provided at the downstream side of the pair of acceleration electrodes.

7. The high-energy ion implanter according to claim 2, wherein in the beam collimator, an incident electrode and an emission electrode of the beam collimator are both grounded so that the energy of the ion beam scanned by the beam scanner is equal to the energy of the ion beam collimated by the pair of acceleration electrodes and the pair of deceleration electrodes, an exit side electrode of an acceleration gap and an entrance side electrode of a deceleration gap are set to the same negative potential, and an exit side electrode of a deceleration gap and an entrance side electrode of an acceleration gap are set to the same positive potential.

8. The high-energy ion implanter according to claim 2, wherein in the acceleration-deceleration electrode lens group, a first pair of acceleration electrodes, a first pair of deceleration electrodes, a second pair of acceleration electrodes, a second pair of deceleration electrodes, ..., an n-th (n is a natural number) pair of acceleration electrodes, and an n-th pair of deceleration electrodes are disposed in this order along the beamline in which the scanned ion beam is incident to the beam collimator and is emitted therefrom,
    wherein a first potential of an entrance side electrode of the first pair of acceleration electrodes is set to a ground potential,
    wherein second potentials of an exit side electrode of the first pair of acceleration electrodes and an entrance side electrode of the first pair of deceleration electrodes are set to −V1[V] (V1>0),
    wherein third potentials of an exit side electrode of the first pair of deceleration electrodes and an entrance side electrode of the second pair of acceleration electrodes are set to V2[V] (V2>0),
    wherein fourth potentials of an exit side electrode of the second pair of acceleration electrodes and an entrance side electrode of the second pair of deceleration electrodes are set to −V1[V] (V1>0),
    wherein fifth potentials of an exit side electrode of the second pair of deceleration electrodes and an entrance side electrode of the third pair of acceleration electrodes are set to V2[V] (V2>0), and wherein a (2n+1)-th potential of an exit side electrode of the n-th pair of acceleration electrodes is set to a ground potential.

9. The high-energy ion implanter according to claim 8, wherein the second potentials and the third potentials satisfy a relation of V1=V2.

10. The high-energy ion implanter according to claim 8, wherein the second potentials and the third potentials satisfy a relation of V1≠V2.

11. The high-energy ion implanter according to claim 8, wherein in the multiple pairs of acceleration electrodes and the multiple pairs of deceleration electrodes, a ground electrode corresponding to an incident entrance and disposed at the most upstream side of the beamline and a first electrode adjacent to the ground electrode form a first suppression electrode unit that suppresses the inflow of electrons, and a ground electrode corresponding to an emission exit and disposed at the most downstream side of the beamline and a second electrode adjacent to the ground electrode form a second suppression electrode unit that suppresses the inflow of electrons.

12. The high-energy ion implanter according to claim 2, wherein in the acceleration-deceleration electrode lens group, a first pair of acceleration electrodes, a first pair of deceleration electrodes, a second pair of acceleration electrodes, a second pair of deceleration electrodes, . . . , an n-th (n is a natural number) pair of acceleration electrodes, and an n-th pair of deceleration electrodes are disposed in this order along the beamline in which the scanned ion beam is incident to the beam collimator and is emitted therefrom,
wherein a first potential of an entrance side electrode of the first pair of acceleration electrodes is set to an inlet potential,
wherein second potentials of an exit side electrode of the first pair of acceleration electrodes and an entrance side electrode of the first pair of deceleration electrodes are set to −V1[V] (V1>0),
wherein third potentials of an exit side electrode of the first pair of deceleration electrodes and an entrance side electrode of the second pair of acceleration electrodes are set to V2[V] (V2>0),
wherein fourth potentials of an exit side electrode of the second pair of acceleration electrodes and an entrance side electrode of the second pair of deceleration electrodes are set to −V1[V] (V1>0),
wherein fifth potentials of an exit side electrode of the second pair of deceleration electrodes and an entrance side electrode of the third pair of acceleration electrodes are set to V2[V] (V2>0), and
wherein a (2n+1)-th potential of an exit side electrode of the n-th pair of acceleration electrodes is set to an outlet potential, wherein both of the inlet potential and the outlet potential are different from V1 or V2.

13. The high-energy ion implanter according to claim 2, wherein the downstream electrode of the beamline of the pair of acceleration electrodes and the upstream electrode of the beamline of the pair of deceleration electrodes are configured as different electrodes.

14. The high-energy ion implanter according to claim 2, wherein the downstream electrode of the pair of acceleration electrodes and the upstream electrode of the pair of deceleration electrodes are configured as different electrodes and are electrically connected to each other.

15. The high-energy ion implanter according to claim 2, wherein the downstream electrode of the pair of deceleration electrodes and the upstream electrode of the pair of acceleration electrodes are configured as different electrodes.

16. The high-energy ion implanter according to claim 2, wherein the downstream electrode of the pair of deceleration electrodes and the upstream electrode of the pair of acceleration electrodes are configured as different electrodes and are electrically connected to each other.

17. The high-energy ion implanter according to claim 2, wherein the downstream electrode of the pair of acceleration electrodes and the upstream electrode of the pair of deceleration electrodes are configured as an integrally continuous electrode unit while both ends thereof are connected to each other.

18. The high-energy ion implanter according to claim 1, wherein the energy of the ion beam immediately before incident to the beam collimator and the energy of the ion beam immediately after emitted from the beam collimator are set to be equal to each other.

19. The high-energy ion implanter according to claim 18, wherein an incident electrode and an emission electrode of the beam collimator are set to a ground potential.

\* \* \* \* \*